(12) United States Patent
Cummings et al.

(10) Patent No.: US 6,689,574 B1
(45) Date of Patent: Feb. 10, 2004

(54) ASSAYS FOR NUCLEAR RECEPTOR AGONISTS AND ANTAGONISTS USING FLUORESCENCE RESONANCE ENERGY TRANSFER

(75) Inventors: Richard T. Cummings, Fanwood, NJ (US); David E. Moller, Watchung, NJ (US); Jeffrey D. Hermes, Warren, NJ (US); Gaochao Zhou, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 525 days.

(21) Appl. No.: 09/166,265

(22) Filed: Oct. 5, 1998

Related U.S. Application Data
(60) Provisional application No. 60/061,385, filed on Oct. 7, 1997.

(51) Int. Cl.$^7$ .................. G01N 33/53; G01N 33/533; G01N 33/566
(52) U.S. Cl. ................ 435/7.8; 435/7.1; 435/7.2
(58) Field of Search ................... 435/7.8, 7.1, 7.2

(56) References Cited

U.S. PATENT DOCUMENTS

| | | | |
|---|---|---|---|
| 4,520,110 A | 5/1985 | Stryer et al. | 436/501 |
| 4,542,104 A | 9/1985 | Stryer et al. | 436/536 |
| 5,162,508 A | 11/1992 | Lehn et al. | 534/15 |
| 5,346,996 A | 9/1994 | Lehn et al. | 534/15 |
| 5,457,185 A | 10/1995 | Lehn et al. | 534/15 |
| 5,534,622 A | 7/1996 | Lehn et al. | 534/15 |

FOREIGN PATENT DOCUMENTS

| | | |
|---|---|---|
| WO | WO 89/05813 | 6/1989 |
| WO | WO 96/30540 | 10/1996 |

OTHER PUBLICATIONS

O'Shea, et al., "Preferential Heterodimer Formation by Isolated Leucine Zippers from Fos and Jun", Science, vol. 245, Aug. 11, 1989, pp. 646–648.
GenBank, Accession No. L07592, Apr. 27, 1993.
GenBank, Accession No. L02932, Jul. 26, 1993.
GenBank, Accession No. U47741, Sep. 29, 1997.
GenBank, Accession No. L40904, Nov. 1, 1995.
Handbook from a course entitled "Basic HFTR Chemistry Training", given Oct. 21–24, 1996 in Franceby Packard, Inc. to Merck & Co., Inc. employees.
Voegel, et al., "TIF2, a 160 kDa transcriptional mediator for the ligand–dependent activation function AF–2 of nuclear receptors", The EMBO Journal, vol. 15, No. 14, pp. 3667–3675, 1996.
Voegel, et al., "The coactivator TIF2 contains three nuclear receptor–binding motifs and mediates . . . ", The EMBO Journal, vol. 17, No. 2, pp. 207–519, 1998.
Janknecht, et al., "Transcriptional control: Versatile molecular glue", Current Biology vol. 6, No. 8, pp. 951–954, 1996.
Torchia, et al., "The transcriptional co–activator p/CIP binds CBP and mediates nuclear–receptor function", Nature, vol. 387, pp. 677–684, Jun. 12, 1997.
Smith, et al., "Coactivator and Corepressor Regulation of the Agonist/Antagonist Activity of the Mixed . . . ", Molecular Endocrinology, vol. 11, No. 6, pp. 657–666, 1997.
Glass, "Some new twists in the regulation of gene expression by thyroid hormone and retinoic acid receptors", J. of Endocrinology, vol. 150, pp. 347–357, 1996.
Mangelsdorf, et al., "The Nuclear Receptor Superfamily: The Second Decade", Cell, vol. 83, pp. 835–839, Dec. 15, 1995.
Castillo, et al., "A Divergent Role of COOH–Terminal Domains in Nurr1 and Nur77 Transactivation", Gene Expreession, vol. 7, pp. 1–12, 1998.
Elbrecht, et al., "Molecular Cloning, Expression and Characterization of Human Peroxisome Proliferation . . . ", Biochem. and Biophys. Res. Comm., vol. 224, pp. 431–437, 1996.
Guan, et al., "Eukaryotic Proteins Expressed in *Escherichia coli:* An Improved Thrombin Cleavage and Purification . . . ", Analytical Biochem., vol. 192, pp. 262–267, 1991.
Sher, et al., "cDNA Cloning, Chromosomal Mapping, and Functional Characterization of the Human . . . ", Biochemistry, vol. 32, pp. 5598–5604, 1993.
Eckner, et al., "Molecular cloning and functional anaysis of the adenovirus E1A–associated 300–kD protein . . . ", Genes & Development, vol. 8, pp. 869–884, 1994.
LeDouarin, et al., "The N–terminal part of TIF1, a putative mediator of the ligand–dependent activation function . . . ", The EMBO Journal, vol. 14, No. 9, pp. 2020–2033, 1995.
Cavailles, et al., "Nuclear factor RIP140 modulates transcriptional activation by the estrogen receptor", THe EMBO Journal, vol. 14, No. 15, pp. 3741–3751, 1995.
Schmidt, et al., "Identification of a New Member of the Steroid Hormone Receptor Superfamily . . . ", Molecular Endocrinology, vol. 6, No. 4, pp. 1634–1641.
Qi, et al., "The Ligand–Binding Domains of the Thyroid Hormone/Retinoid Receptor Gene Subfamily . . . ", Molecular and Cellular Biology, vol. 15, No. 3, pp. 1817–1825, Varch 1995.
Kwok, et al., "Nuclear protein CBP is a coactivator for the transcription factor CREB", Nature, vol. 370, pp. 223–226, Jul. 21, 1994.

(List continued on next page.)

*Primary Examiner*—Michael Pak
(74) *Attorney, Agent, or Firm*—Jack L. Tribble

(57) ABSTRACT

Provided is a method of identifying agonists and antagonists of nuclear receptors that comprises measuring agonist-dependent fluorescence resonance energy transfer (FRET) between a fluorescently labeled nuclear receptor or ligand binding domain and fluorescently labeled CREB-binding protein (CBP), p300, other nuclear co-activator, or binding portion thereof. The method is simple, rapid, and inexpensive. Nuclear receptors and nuclear receptor co-activators labeled with fluorescent reagents for use in the above-described method are also provided.

23 Claims, 11 Drawing Sheets

OTHER PUBLICATIONS

Alberts, et al., "Activation of cAMP and mitogen responsive genes relies on a common nuclear factor", Nature, vol. 370, pp. 226–229, Jul. 21, 1994.

Lee, et al., "Interaction of thyroid–hormone receptor with a conserved transcriptional mediator", Nature, vol. 374, pp. 91–94, Mar. 2, 1995.

Borrow, et al., "The translocation t(8;16)(p11;p13) of acute myeloid leukaemia fuses a putative . . . ", Nature Genetics, vol. 14 Sep 1996, pp. 33–41.

Hanstein, et al., "p300 is a component of an estrogen receptor coactivator complex", Proc. Natl. Acad. Sci. USA, vol. 93, pp. 11540–11545, Oct. 1996.

Yao, et al., "The nuclear hormone receptor coactivator SRC–1 is a specific target of p300", vol. 93, No. 10626–10631, Oct. 1996.

Onate, et al., "Sequence and Characterization of a Coactivator for the Steroid Hormone Receptor Superfamily", Science, vol. 270, pp. 1354–1357, Nov. 24, 1995.

DiRenzo, "Peroxisome Proliferator–Activated Receptors and Retinoic Acid Receptors Differentially . . . ", vol. 17, No. 4, pp. 2166–2176.

Montminy, "Something new to hand your HAR on", Nature, vol. 387, pp. 654–655, Jun. 12, 1997.

Gansow, et al., Synthesis and Chemical Properties of Lanthanide Cryptates, Journal of the American Chemical Society, 99:21, Oct. 12, 1977.

Sabbatini, et al., "Luminescence of lanthanide cryptates: effects of phosphate and iodide anions", Journal of Alloys and Compunds, vol. 180, pp. 363–367 (1992).

Lehn, et al., "56. Synthesis and Properties of Sodium and Europium (III) Cryptates incorporating . . . ", Helvetica Chemica, vol. 74, pp. 572–578, 1991.

Mathis, et al., "Amplified Homogeneous Time Resolved Immunofluorometric Assay of Prolactin", Clinical Chemistry, vol. 39, No. 6, pp. 1251, 1993.

Lehn, et al., "10. Synthesis and Properties of Acyclic and Cryptate Europium (II) Complexes Incorporating . . . ", Helvetica Chimica Acta, vol. 73, pp. 106–111, 1990.

Mathis, "Rare Earth Cryptates and Homogenous Fluoroimmunoassays with Human Sera", Clinical Chemistry, vol. 39, No. 9, pp. 1953–1959, 1993.

Oi, et al., "Fluorescent Phycobiliprotein Conjugates for Analyses of Cells and Molecules", The Journal of Cell Biology, vol. 93, pp. 981–986, Jun. 1982.

Karin, "New Twists in Gene Gene Regulation by Glucocorticoid Receptor: Is DNA Binding Dispensable?", Cell, vol. 93, pp. 487–490, May 1998.

Feng, et al., "Hormone–Dependent Coactivator Binding to a Hydrophobic Cleft on Nuclear Receptors", Science, vol. 280, pp. 1747–1714, Jun. 12, 1998.

Elstner, et al., "Ligands for peroxisome proliferation–activated receptor gamma and retinoic acid receptor inhibit . . . ", Proc.Natl. Acad. Sci. USA, vol. 95, pp. 8806–8811, Jul. 1998.

Zhou, et al., "Role of peroxisome proliferator–activated receptor alpha in a disease of pancreatic beta cells", Proc. Natl. Acad. Sci. USA, vol. 95, pp. 8898–8903, Jul. 1998.

Shiau, et al., "The Structural Basis of Estrogen Receptor/Coactivator Recognition and the Antagonism . . . ", Cell, vol. 95, pp. 927–937, Dec. 23, 1998.

Hanstein, et al., "p300 is a component of an estrogen receptor coactivator complex", Proc. Natl. Acad. Sci. USA, vol. 93, pp. 11540–11545, Oct. 1996.

Kamei, et al., "A CBP Integrator Complex Madiates Transcriptional Activation and AP–1 Inhibition . . . ", Cell, vol. 85, pp. 403–414, 1996.

Chakravarti, et al., Role of CBP/P300 in nuclear receptor signalling, Nature, vol. 383, pp. 99–103, Sep. 5, 1996.

Heery, et qal., "A signature motif in transcriptional co–activators mediates binding to nuclear receptors", Nature, vol. 387, pp. 733–736, Jun. 12, 1997.

Clegg, "Fluorescence resonance energy transfer,", Current Opinion in Biotechnology, vol. 6, pp. 103–110, 1995.

Alpha, et al., "Energy Transfer Luminescence of Europium (III) and Terbium (III) Cryptates of Macrobicyclic Polypyridine Ligands", Angew. Chem. Int. Ed. Engl., vol. 26, No. 3, pp. 266–267, 1987.

Mathis, et al., "Probing Molecular Interactions with Homogeneous Techniques Based on Rare Earth Cryptates . . . ", Clin. Chem., vol. 49, No. 9, pp. 1391–1397, 1995.

Prat, et al., "Europium (III) Cryptate: A Fluorescent Label for the Detection of DNA Hybrids on Solid Support", Analytical Biochemistry, vol. 195, pp. 283–289, 1991.

Lopez, et al., "Europium (III) Trisbipyridine Cryptate Label for Time–Resolved Fluorescence Detection . . . ", Clin. Chem., vol. 39, No. 2, pp. 196–201, 1993.

Kronick, "The use of phycobiliproteins as fluorescent labels in immunoassay", Journal of Immunological Methods, vol. 92, pp. 1–13, 1986.

Elbrecht, et al., "Molecular Cloning, Expression and Characterization of Human Peroxisome Proliferator . . . ", Biochem. and Biophys. Res. Comm., vol. 224, pp. 431–437, 1996.

```
1    MAENLLDGPPNPKRAKLSSPGFSANDSTDFGSLFDLENDLPDELIPNGGELGLLNSGNLV
61   PDAASKHKQLSELLRGGSGSSINPGIGNVSASSPVQQGLGGQAQGQPNSANMASLSAMGK
121  SPLSQGDSSAPSLPKQAASTSGPTPAASQALNPQAQKQVGLATSSPATSQTGPGICMNAN
181  FNQTHPGLLNSNSGHSLINQASQGQAQVMNGSLGAAGRGRGAGMPYPTPAMQGASSSVLA
241  ETLTQVSPQMTGHAGLNTAQAGGMAKMGITGNTSPFGQPFSQAGGQPMGATGVNPQLASK
301  QSMVNSLPTFPTDIKNTSVTNVPNMSQMQTSVGIVPTQAIATGPTADPEKRKLIQQQLVL
361  LLHAHKCQRREQANGEVRACSLPHCRTMKNVLNHMTHCQAGKACQ
```

FIG. 7A

```
1     cgagccccga ccccgtccg  ggccctcgcc ggccgcgccg cccgtgcccg gggctgtttt
61    cccgagcagg tgaaaatggc tgagaacttg ctggacggac cgcccaaccc caaaagagcc
121   aaactcagct cgcccggttt ctcggcgaat gacagcacag attttggatc attgtttgac
181   ttggaaaatg atcttcctga tgagctgata cccaatggag gagaattagg ccttttaaac
241   agtgggaacc ttgttccaga tgctgcttcc aaacataaac aactgtcgga gcttctacga
301   ggaggcagcg gctctagtat caacccagga ataggaaatg tgagcgccag cagccccgtg
361   cagcagggcc tgggtggcca ggctcaaggg cagccgaaca gtgctaacat ggccagcctc
421   agtgccatgg gcaagagccc tctgagccag ggagattctt cagcccccag cctgcctaaa
481   caggcagcca gcacctctgg gcccacccc gctgcctccc aagcactgaa tccgcaagca
541   caaaagcaag tggggctggc gactagcagc cctgccacgt cacagactgg acctggtatc
601   tgcatgaatg ctaactttaa ccagacccac ccaggcctcc tcaatagtaa ctctggccat
661   agcttaatta atcaggcttc acaagggcag gcgcaagtca tgaatggatc tcttggggct
721   gctggcagag gaaggggagc tggaatgccg taccctactc cagccatgca gggcgcctcg
781   agcagcgtgc tggctgagac cctaacgcag gtttccccgc aaatgactgg tcacgcggga
841   ctgaacaccg cacaggcagg aggcatggcc aagatgggaa taactgggaa cacaagtcca
901   tttggacagc ctttagtca agctggaggg cagccaatgg gagccactgg agtgaacccc
961   cagttagcca gcaaacagag catggtcaac agtttgccca ccttccctac agatatcaag
1021  aatacttcag tcaccaacgt gccaaatatg tctcagatgc aaacatcagt gggaattgta
1081  cccacacaag caattgcaac aggccccact gcagatcctg aaaaacgcaa actgatacag
1141  cagcagctgg ttctactgct tcatgctcat aagtgtcaga gacgagagca agcaaacgga
1201  gaggttcggg cctgctcgct cccgcattgt cgaaccatga aaaacgtttt gaatcacatg
1261  acgcattgtc aggctgggaa agcctgccaa
```

FIG. 7B

```
  1 MVDTESPLCPLSPLEAGDLESPLSEEFLQEMGNIQEISQSIGEDSSGSFGFTEYQYLGSC
 61 PGSDGSVITDTLSPASSPSSVTYPVVPGSVDESPSGALNIECRICGDKASGYHYGVHACE
121 GCKGFFRRTIRLKLVYDKCDRSCKIQKKNRNKCQYCRFHKCLSVGMSHNAIRFGRMPRSE
181 KAKLKAEILTCEHDIEDSETADLKSLAKRIYEAYLKNFNMNKVKARVILSGKASNNPPFV
241 IHDMETLCMAEKTLVAKLVANGIQNKEVEVRIFHCCQCTSVETVTELTEFAKAIPAFANL
301 DLNDQVTLLKYGVYEAIFAMLSSVMNKDGMLVAYGNGFITREFLKSURKPFCDIMEPKFD
361 FAMKFNALELDDSDISLFVAAIICCGDRPGLLNVGHIEKMQEGIVHVURLHLQSNHPDDI
421 FLPKLLQKMADLRQLVTEHAQLVQIIKKTESDAALHPLLQEIYRDMY
```

FIG.8A

```
   1    ggcccaggct gaagctcagg gccctgtctg ctctgtggac tcaacagttt gtggcaagac
  61    aagctcagaa ctgagaagct gtcaccacag ttctggaggc tgggaagttc aagatcaaag
 121    tgccagcaga ttcagtgtca tgtgaggacg tgcttcctgc ttcatagata agagtagctt
 181    ggagctcggc ggcacaacca gcaccatctg gtcgcgatgg tggacacgga agcccactc
 241    tgccccctct ccccactcga ggccggcgat ctagagagcc cgttatctga agagttcctg
 301    caagaaatgg gaaacatcca agagatttcg caatccatcg gcgaggatag ttctggaagc
 361    tttggctta  cggaataccag tatttagga agctgtcctg ctcagatgg ctcggtcatc
 421    acggacacgc tttcaccagc ttcgagcccc tcctcggtga cttatcctgt ggtccccggc
 481    agcgtggacg agtctcccag tggagcattg aacatcgaat gtagaatctg cggggacaag
 541    gcctcaggct atcattacgg agtccacgcg tgtgaaggct gcaagggctt ctttcggcga
 601    acgattcgac tcaagctggt gtatgacaag tgcgaccgca gctgcaagat ccagaaaaag
 661    aacagaaaca atgccagta ttgtcgattt cacaagtgcc tttctgtcgg gatgtcacac
 721    aacgcgattc gttttggacg aatgccaaga tctgagaaag caaaactgaa agcagaaatt
 781    cttacctgtg aacatgacat agaagattct gaaactgcag atctcaaatc tctggccaag
 841    agaatctacg aggcctactt gaagaacttc aacatgaaca aggtcaaagc ccgggtcatc
 901    ctctcaggaa aggccagtaa caatccacct tttgtcatac atgatatgga gacactgtgt
 961    atggctgaga gacgctggt ggccaagctg gtggccaatg catccagaa caaggaggtg
1021    gaggtccgca tctttcactg ctgccagtgc acgtcagtgg agaccgtcac ggagctcacg
1081    gaattcgcca aggccatccc agcgttcgca aacttggacc tgaacgatca agtgacattg
1141    ctaaaatacg gagtttatga ggccatattc gccatgctgt cttctgtgat gaacaaagac
1201    gggatgctgg tagcgtatgg aaatgggttt ataactcgtg aattcctaaa aagcctaagg
1261    aaaccgttct gtgatatcat ggaacccaag tttgattttg ccatgaagtt caatgcactg
1321    gaactggatg acagtgatat ctccctttt gtggctgcta tcatttgctg tggagatcgt
1381    cctggccttc taaacgtagg acacattgaa aaaatgcagg agggtattgt acatgtgctc
1441    agactccacc tgcagagcaa ccacccggac gatatctttc tcttcccaaa acttcttcaa
1501    aaaatggcag acctccggca gctggtgacg gagcatgcgc agctggtgca gatcatcaag
1561    aagacggagt cggatgctgc gctgcacccg ctactgcagg agatctacag ggacatgtac
1621    tgagttcctt cagatcagcc acaccttttc aggagttct gaagctgaca gcactacaaa
1681    ggagacgggg gagcagcacg attttgcaca aatatccacc actttaacct tagagcttgg
1741    acagtctgag ctgtaggtaa ccggcatatt attccatatc tttgttttaa ccagtacttc
1801    taagagcata gaactcaaat gctgggggag gtggctaatc tcaggactgg gaag
```

FIG.8B

```
1    MTMVDTEIAFWPTNFGISSVDLSVMEDHSHSFDIKPFTTVDFSSISTPHYEDIPFTRTDP
61   VVADYKYDLKLQEYQSAIKVEPASPPYYSEKTQLYNKPHEEPSNSLMAIECRVCGDKASG
121  FHYGVHACEGCKGFFRRTIRLKLIYDRCDLNCRIHKKSRNKCQYCRFQKCLAVGMSHNAI
181  RFGRIAQAEKEKLLAEISSDIDQLNPESADLRQALAKHLYDSYIKSFPLTKAKARAILTG
241  KTTDKSPFVIYDMNSLMMGEDKIKFKHITPLQEQSKEVAIRIFQGCQFRSVEAVQEITEY
301  AKSIPGFVNLDLNDQVTLLKYGVHEIIYTMLASLMNKDGVLISEGQQGFMTREFLKSLRKP
361  FGDFMEPKFEFAVKFNALELDDSDLAIFIAVIILSGDRPGLLNVKPIEDIQDNLLQALEL
421  QLKLNHPESSQUAKLLQKMTDLRQIVTEHVQLLQVIKKTETDMSLHPLLQEIYKDLY
```

FIG.9A

```
1     ccgaccttac cccaggcggc cttgacgttg gtcttgtcgg caggagacag caccatggtg
61    ggttctctct gagtctggga attcccgagc ccgagccgca gccgccgcct gggggggcttg
121   ggtcggcctc gaggacaccg gagaggggcg ccacgccgcc gtggccgcag aaatgaccat
181   ggttgacaca gagatcgcat tctggcccac caactttggg atcagctccg tggatctctc
241   cgtaatggaa gaccactccc actcctttga tatcaagccc ttcactactg ttgacttctc
301   cagcatttct actccacatt acgaagacat tccattcaca agaacagatc cagtggttgc
361   agattacaag tatgacctga aacttcaaga gtaccaaagt gcaatcaaag tggagcctgc
421   atctccacct tattattctg agaagactca gctctacaat aagcctcatg aagagccttc
481   caactccctc atggcaattg aatgtcgtgt ctgtggagat aaagcttctg gatttcacta
541   tggagttcat gcttgtgaag gatgcaaggg tttcttccgg agaacaatca gattgaagct
601   tatctatgac agatgtgatc ttaactgtcg gatccacaaa aaagtagaa ataaatgtca
661   gtactgtcgg tttcagaaat gccttgcagt ggggatgtct cataatgcca tcaggtttgg
721   gcggatcgca caggccgaga aggagaagct gttggcggag atctccagtg atatcgacca
781   gctgaatcca gagtccgctg acctccgtca ggccctggca aacatttgt atgactcata
841   cataaagtcc ttcccgctga ccaaagcaaa ggcgagggcg atcttgacag gaaagacaac
901   agacaaatca ccattcgtta tctatgacat gaattcctta atgatgggag aagataaaat
961   caagttcaaa cacatcaccc cctgcagga gcagagcaaa gaggtggcca tccgcatctt
1021  tcagggctgc cagtttcgct ccgtggaggc tgtgcaggag atcacagagt atgccaaaag
1081  cattcctggt tttgtaaatc ttgacttgaa cgaccaagta actctcctca aatatggagt
1141  ccacgagatc atttacacaa tgctggcctc cttgatgaat aaagatgggg ttctcatatc
1201  cgagggccaa ggcttcatga agggagtt ctaaagagc tgcgaaagc ttttggtga
1261  ctttatggag cccaagtttg agtttgctgt gaagttcaat gcactggaat tagatgacag
1321  cgacttggca atatttattg ctgtcattat tctcagtgga gaccgcccag gtttgctgaa
1381  tgtgaagccc attgaagaca ttcaagacaa cctgctacaa gccctggagc tccagctgaa
1441  gctgaaccac cctgagtcct cacagctgtt tgccaagctg ctccagaaaa tgacagacct
1501  cagacagatt gtcacggaac acgtgcagct actgcaggtg atcaagaaga cggagacaga
1561  catgagtctt cacccgctcc tgcaggagat ctacaaggac ttgtactagc agagagtcct
1621  gagccactgc aacatttcc cttcttccag ttgcactatt ctgagggaaa atctgaccat
1681  aagaaattta ctgtgaaaaa gcgttttaaa aagaaaaggg tttagaatat gatctatttt
1741  atgcatattg tttataaaga cacatttaca atttactttt aatattaaaa attaccatat
1801  tatgaaattg c
```

FIG.9B

```
  1  MEQPQEEAPEVREEEEKEEVAEAEGAPELNGGPQHALPSSSYTDLSRSSSPPSLLDQLQM
 61  GCPGASCGSLNMECRVCGDKASGFHYGVHACEGCKGFFRRTIRMKLEYEKCERSCKIQKK
121  NRNKCQYCRFQKCLALGMSHNAIRFGRMPEAEKRKLVAGLTANEGSQYNPQVADLKAFSK
181  HIYNAYLKNFNMTKKKARSILTGKASHTAPFVIHDIETLWQAEKGLVWKQLVNGLPPYKE
241  ISVHVFYRCQCTTVETVRELTEFAKSIPSFSSLFLNDQVTLLKYGVHEAIFAMLASIVNK
301  DGLLVANGSGFVTREFLRSLRKPFSDIIEPKFEFAVKFNALELDDSDLALFIAAIILCGD
361  RPGLMNVPRVEAIQDTILRALEFHLQANHPDAQYLFPKLLQKMADLRQLVTEHAQMMQRI
421  KKTETETSLHPLLQEIYKDMY
```

FIG.10A

```
   1  gaattctgcg gagcctgcgg gacggcggcg ggttggcccg taggcagccg ggacagtgtt
  61  gtacagtgtt ttgggcatgc acgtgatact cacacagtgg cttctgctca ccaacagatg
 121  aagacagatg caccaacgag ggtctggaat ggtctggagt ggtctggaaa gcagggtcag
 181  atacccctgg aaaactgaag cccgtggagc aatgatctct acaggactgc ttcaaggctg
 241  atgggaacca ccctgtagag gtccatctgc gttcagaccc agacgatgcc agagctatga
 301  ctgggcctgc aggtgtggcg ccgaggggag atcagccatg gagcagccac aggaggaagc
 361  ccctgaggtc cgggaagagg aggagaaaga ggaagtggca gaggcagaag gagccccaga
 421  gctcaatggg ggaccacagc atgcacttcc ttccagcagc tacacagacc tctcccggag
 481  ctcctcgcca ccctcactgc tggaccaact gcagatgggc tgtgacgggg cctcatgcgg
 541  cagcctcaac atggagtgcc gggtgtgcgg ggacaaggca tcgggcttcc actacggtgt
 601  tcatgcatgt gagggggtgca agggcttctt ccgtcgtacg atccgcatga agctggagta
 661  cgagaagtgt gagcgcagct gcaagattca aagaagaac cgcaacaagt gccagtactg
 721  ccgcttccag aagtgcctgg cactgggcat gtcacacaac gctatccgtt ttggtcggat
 781  gccggaggct gagaagagga agctggtggc agggctgact gcaaacgagg ggagccagta
 841  caacccacag gtggccgacc tgaaggcctt ctccaagcac atctacaatg cctacctgaa
 901  aaacttcaac atgaccaaaa agaaggcccg cagcatcctc accggcaaag ccagccacac
 961  ggcgcccttt gtgatccacg acatcgagac attgtggcag gcagagaagg ggctggtgtg
1021  gaagcagttg gtgaatggcc tgcctcccta caaggagatc agcgtgcacg tcttctaccg
1081  ctgccagtgc accacagtgg agaccgtgcg ggagctcact gagttcgcca gagcatccc
1141  cagcttcagc agcctcttcc tcaacgacca ggttacccttctcaagtatg cgtgcacga
1201  ggccatcttc gccatgctgg cctctatcgt caacaaggac gggctgctgg tagccaacgg
1261  cagtggcttt gtcacccgtg agttcctgcg cagcctccgc aaacccttca gtgatatcat
1321  tgagcctaag tttgaatttg ctgtcaagtt caacgccctg gaacttgatg acagtgacct
1381  ggccctattc attgcggcca tcattctgtg tggagaccgg ccaggcctca tgaacgttcc
1441  acgggtggag gctatccagg acaccatcct gcgtgccctc gaattccacc tgcaggccaa
1501  ccaccctgat gcccagtacc tcttccccaa gctgctgcag aagatggctg acctgcggca
1561  actggtcacc gagcacgccc agatgatgca gcggatcaag aagaccgaaa ccpagacctc
1621  gctgcaccct ctgctccagg agatctacaa ggacatgtac taacggcggc acccaggcct
1681  ccctgcagac tccaatgggg ccagcactgg aggggcccac ccacatgact tttccattga
1741  ccagctctct tcctgtcttt gttgtctccc tctttctcag ttcctctttc ttttctaatt
1801  cctgttgctc tgtttcttcc tttctgtagg tttctctctt cccttctccc ttctcccttg
1861  ccctcccttt ctctctccta tccccacgtc tgtcctcctt tcttattctg tgagatgttt
1921  tgtattattt caccagcagc atagaacagg acctctgctt ttgcacacct ttccccagg
1981  agcagaagag agtgggcctg ccctctgccc catcattgca cctgcaggct taggtcctca
2041  cttctgtctc ctgtcttcag agcaaaagac ttgagccatc aaagaaaca ctaagctctc
2101  tgggcctggg ttccagggaa ggctaagcat ggcctggact gactgcagcc ccctatagtc
2161  atggggtccc tgctgcaaag acagtggca gacccggca gtagagccga gatgcctccc
2221  caagactgtc attgccctc cgatcgtgag gccacccact gacccaatga tcctctccag
2281  cagcacacct cagccccact gacacccagt gtccttccat cttcacactg gtttgccagg
2341  ccaatgttgc tgatggcccc tccagcacac acacataagc actgaaatca ctttacctgc
2401  aggcaccatg cacctccctt ccctccctga ggcaggtgag aacccagaga gaggggcctg
```

FIG.10B

```
2461 caggtgagca ggcagggctg ggccaggtct ccggggaggc aggggtcctg caggtcctgg
2521 tgggtcagcc cagcacctcg cccagtggga gcttcccggg ataaactgag cctgttcatt
2581 ctgatgtcca tttgtcccaa tagctctact gccctcccct tcccctttac tcagcccagc
2641 tggccaccta gaagtctccc tgcacagcct ctagtgtccg gggaccttgt gggaccagtc
2701 ccacaccgct ggtccctgcc ctccctgct cccaggttga ggtgcgctca cctcagagca
2761 gggccaaagc acagctgggc atgccatgtc tgagcggcgc agagccctcc aggcctgcag
2821 gggcaagggg ctggctggag tctcagagca cagaggtagg agaactgggg ttcaagccca
2881 ggcttcctgg gtcctgcctg gtcctccctc ccaaggagcc attctatgtg actctgggtg
2941 gaagtgccca gcccctgcct gacggnnnnn nngatcactc tctgctggca ggattcttcc
3001 cgctccccac ctacccagct gatgggggtt ggggtgcttc tttcagccaa ggctatgaag
3061 ggacagctgc tgggacccac ctccccccctt ccccggccac atgccgcgtc cctgccccca
3121 cccgggtctg gtgctgagga tacagctctt ctcagtgtct gaacaatctc caaaattgaa
3181 atgtatattt ttgctaggag ccccagcttc ctgtgttttt aatataaata gtgtacacag
3241 actgacgaaa ctttaaataa atgggaatta aatatttaaa aaaaaaagcg ccgcgaatt
3301 c
```

FIG.10C

ASSAYS FOR NUCLEAR RECEPTOR AGONISTS AND ANTAGONISTS USING FLUORESCENCE RESONANCE ENERGY TRANSFER

CROSS-REFERENCE TO RELATED APPLICATIONS

This application claims the benefit of U.S. Provisional Application No. 60/061,385, filed Oct. 7, 1997, the contents of which are incorporated herein by reference in their entirety.

STATEMENT REGARDING FEDERALLY-SPONSORED R&D

Not applicable.

REFERENCE TO MICROFICHE APPENDIX

Not applicable.

FIELD OF THE INVENTION

This invention relates to methods of identifying novel agonists and antagonists of nuclear receptors utilizing the agonist-dependent interaction of such receptors with CREB-binding protein (CBP) or other nuclear receptor co-activators in which this interaction is detected by fluorescence resonance energy transfer.

BACKGROUND OF THE INVENTION

Nuclear receptors are a superfamily of ligand-activated transcription factors that bind as homodimers or heterodimers to their cognate DNA elements in gene promoters. The superfamily, with more than 150 members, can be divided into subfamilies (e.g. the steroid, retinoid, thyroid hormone, and peroxisome proliferator-activated [PPAR] subfamilies). Each subfamily may consist of several members which are encoded by individual genes (e.g. PPARα, PPARγ, and PPARδ). In addition, alternative mRNA splicing can result in more than one isoform of these genes as in the case of specific PPARs (e.g. PPARγ1 and PPARγ2). The nuclear receptor superfamily is involved in a wide variety of physiological functions in mammalian cells: e.g., differentiation, proliferation, and metabolic homeostasis. Dysfunction or altered expression of specific nuclear receptors has been found to be involved in disease pathogenesis.

The PPAR subfamily of nuclear receptors consists of three members: PPARα, PPARγ, and PPARδ. PPARα is highly expressed in liver and kidney. Activation of PPARα by peroxisome proliferators (including hypolipidimic reagents such as fibrates) or medium and long-chain fatty acids is responsible for the induction of acyl-CoA oxidase and hydratase-dehydrogenase (enzymes required for peroxisomal β-oxidation), as well as cytochrome P450 4A6 (an enzyme required for fatty acid o-hydroxylase). Thus, PPARα has an important role in the regulation of lipid metabolism and is part of the mechanism through which hypolipidimic compounds such as fibrates exert their effects. PPARγ is predominantly expressed in adipose tissue. Recently, a prostaglandin J2 metabolite, 15-Deoxy-D12,14-prostaglandin J2, has been identified as a potential physiological ligand of PPARγ. Both 15-Deoxy-D12,14-prostaglandin J2 treatment of preadipocytes or retroviral expression of PPARγ2 in fibroblasts induced adipocyte differentiation, demonstrating the role of PPARγ in adipocyte differentiation and lipid storage. The demonstration that anti-diabetic and lipid-lowering insulin sensitizing compounds known as thiazolidinediones are high affinity ligands for PPARγ suggests a broad therapeutic role for PPARγ ligands in the treatment of diabetes and disorders associated with insulin resistance (e.g. obesity and cardiovascular disease).

Nuclear receptor proteins contain a central DNA binding domain (DBD) and a COOH-terminal ligand binding domain (LBD). The DBD is composed of two highly conserved zinc fingers that target the receptor to specific promoter/enhancer DNA sequences known as hormone response elements (HREs). The LBD is about 200–300 amino acids in length and is less well conserved than the DBD. There are at least three functions for the LBD: dimerization, ligand binding, and transactivation. The transactivation function can be viewed as a molecular switch between a transcriptionally inactive and a transcriptionally active state of the receptor. Binding of a ligand which is an agonist flips the switch from the inactive state to the active state. The COOH-terminal portion of the LBD contains an activation function domain (AF2) that is required for the switch.

The ligand-induced nuclear receptor molecular switch is mediated through interactions with members of a family of nuclear receptor co-activators (e.g., CBP/p300, SRC-1/NcoA-1, TIF2/GRIP-lJNcoA-2, and p/CIP). Upon binding of agonist to its cognate receptor LBD, a conformational change in the receptor protein creates a co-activator binding surface and results in recruitment of co-activator(s) to the receptor and subsequent transcriptional activation. The binding of antagonist ligands to nuclear receptors will not induce the required conformational change and prevents recruitment of co-activator and subsequent induction of transcription. The co-activators CREB-binding protein (CBP) and p300 are two closely related proteins that were originally discovered by virtue of their ability to interact with the transcription factor CREB. These two proteins share extensive amino acid sequence homology. CBP can form a bridge between nuclear receptors and the basic transcriptional machinery (Kamei et al., 1996, Cell 85:403–414; Chakravarti et al., 1996, Nature 383:99–103; Hanstein et al., 1996, Proc. Natl. Acad. Sci. USA 93:11540–11545; Heery et al., 1997, Nature 387:733–736). CBP also contains intrinsic histone acetyltransferase activity which could result in local chromatin rearrangement and further activation of transcription. Ligand- and AF2-dependent interaction between certain nuclear receptors and CBP has been demonstrated in in vitro pull down assays and far-western assays. This interaction is both necessary and sufficient for the transcriptional activation that is mediated by these nuclear receptors. Thus, an AF2 mutant of the estrogen receptor (ER) which abolishes the transcriptonal function of the receptor is incapable of interacting with CBP.

The N-termini of CBP and p300 have been shown to interact with the ligand-binding domains of some nuclear receptors (Kamei et al., 1996, Cell 85:403–414, hereinafter "Kamei"). Kamei was able to demonstrate direct interaction of CBP and p300 with nuclear receptors by several different methods:

(1) Kamei produced GST fusion proteins of the first 100 amino acids of the N-terminus of CBP. These fusion proteins were run out on a polyacrylamide gel, transferred to a membrane, and the membrane was exposed to $^{32}$P-labeled ligand-binding domains of nuclear receptors. In the presence of ligand, a specific binding interaction between the CBP and nuclear receptor fragments was detected in that the $^{32}$P-labeled ligand-binding domains were observed to bind to the bands on the membrane containing the GST-CBP fusion proteins.

(2) Kamei also utilized the yeast two-hybrid system. The ligand-binding domain of the nuclear receptor fused to the DNA-binding domain of the LexA protein was used as bait. The amino terminal domain of CBP fused to the gal4 transactivation domain was used as prey. In the presence of ligand, a specific binding interaction (occurring in vivo, i.e., within the yeast) was observed between the CBP and nuclear receptor fragments.

(3) Kamei observed ligand-induced binding between CBP and nuclear receptors via a gel-shift assay. This assay is based on the observation that, in the presence of ligand, nuclear receptors will bind to oligonucleotides containing their target recognition sequence. Such binding results in the formation of a nuclear receptor-ligand-oligonucleotide complex having a higher molecular weight than the oligonucleotide alone. This difference in molecular weight is detected via a shift in position of the $^{32}$P-labeled oligonucleotide when it is run out on a polyacrylamide gel. Kamei found that a fragment of CBP (the N-terminal 100 amino acids) was capable of binding to the nuclear receptor-ligand-oligonucleotide complex and shifting the complex's position on the gel to an even higher molecular weight.

(4) Kamei was able to co-immunoprecipitate CBP using antibodies to nuclear receptors in extracts from a variety of cells in the presence of ligand.

(5) By the use of transcriptional activation assays, Kamei was able to demonstrate that nuclear receptors and CBP interact in a functional manner. Such transcriptional activation assays can indicate that two proteins are involved in a pathway that results in transcriptional activation but these assays do not prove that the interaction between the proteins is one of direct binding.

By the above-described methods, Kamei was able to demonstrate specific binding interactions between CBP and the retinoic acid receptor (RAR), glucocorticoid receptor (GR), thyroid hormone receptor ($T_3R$), and retinoid X receptor (RXR). Kamei also demonstrated specific binding between the N-terminus of p300 and RAR. However, Kamei did not demonstrate specific binding between CBP, p300, or any other nuclear receptor co-activators and PPARs.

What is striking about the methods used by Kamei is their extremely laborious and time consuming nature. Such methods involve, among other things, the construction of fusion proteins, the preparation of $^{32}$P-labeled proteins, the construction of specialized expression vectors for the yeast two-hybrid assay and the transcriptional activation assays, the running of many gels, and the raising of antibodies. Most of these assays take days to carry out and preparing the reagents needed to carry them out may take weeks. Because of the complicated reagents that are involved in these assays and the time needed to prepare and run the assays, these assays tend to be costly. Investigators other than Kamei who have studied the interaction between nuclear receptors and CBP have also been forced to rely on such cumbersome methods (see, e.g., Chakravarti et al., 1996, Nature 383:99–103; Hanstein et al., 1996, Proc. Natl. Acad. Sci. USA 93:11540–11545; Heery et al., 1997, Nature 387:733–736).

Kamei did not use the above-described methods to identify novel agonists or antagonists of nuclear receptors. The focus of Kamei was not on agonists or antagonists, but rather on the interaction between nuclear receptors and CBP. Although modifying the methods of Kamei to identify agonists or antagonists might be possible, such methods would suffer from serious disadvantages. This is because, as discussed above, all of the assays employed by Kamei to study the interaction of CBP and p300 with nuclear receptors are very laborious, slow, and costly. Given the therapeutic importance of steroid hormones such as estrogen, cortisol, progesterone, and other nuclear receptor agonists such as thyroid hormone and antidiabetic thiazolidinedione compounds, the need for improved high-throughput screening assays to identify potential pharmaceutical compounds affecting nuclear receptors is clear. Historically, therapeutically useful nuclear receptor ligand compounds were identified by screening animal models, an approach which is even more labor intensive and time consuming than the methods used by Kamei. Also, approaches such as those used by Kamei are ill-suited for the identification of antagonists of nuclear receptors. It is now widely appreciated that antagonists of nuclear receptors can be valuable therapeutic agents. Examples of such therapeutically useful antagonists are tamoxifene, raloxifene, and RU-486.

What is needed is a high throughput, time and labor-saving, non-radioactive, inexpensive, and very reliable assay for the identification and characterization of both agonists and antagonists of nuclear receptors. Such an assay is provided by the present invention.

SUMMARY OF THE INVENTION

The present invention provides novel methods of identifying agonists and antagonists of nuclear receptors. The methods take advantage of the agonist-dependent binding of nuclear receptors and CBP, p300, or other nuclear receptor co-activators. In the absence of agonist, binding between the nuclear receptor and CBP, p300, or other nuclear receptor co-activators does not occur. If agonist is present, however, such binding occurs and can be detected by fluorescence resonance energy transfer (FRET) between a fluorescently-labeled nuclear receptor and fluorescently-labeled CBP, p300, or other nuclear receptor co-activator. Antagonists can be identified by virtue of their ability to prevent or disrupt the agonist-induced interaction of nuclear receptors and CBP, p300, or other nuclear receptor co-activators. In contrast to prior art methods of identifying agonists and antagonists of nuclear receptors, the methods of the present invention, are simple, rapid, and less costly.

The present invention provides a nuclear receptor or ligand binding domain thereof labeled with a fluorescent reagent for use in the above-described methods of identifying agonists and antagonists of nuclear receptors. The present invention also provides CBP, p300, or other nuclear receptor co-activator, or a binding portion thereof, labeled with a fluorescent reagent.

BRIEF DESCRIPTION OF THE DRAWINGS

FIG. 7A shows the amino acid sequence of human CBP (SEQ.ID.NO.:1).

FIG. 7B shows the nucleotide sequence of a cDNA encoding human CBP (SEQ.ID.NO.:2). The open reading frame is at positions 76–1290.

FIG. 8A shows the amino acid sequence of human PPARα (SEQ.ID.NO.:3).

FIG. 8B shows the nucleotide sequence of a cDNA encoding human PPARα (SEQ.ID.NO.:4). The open reading frame is at positions 217–1623.

FIG. 9A shows the amino acid sequence of human PPARγ1 (SEQ.ID.NO.:5).

FIG. 9B shows the nucleotide sequence of a cDNA encoding human PPARγ1 (SEQ.ID.NO.:6). The open reading frame is at positions 173–1609.

FIG. 10A shows the amino acid sequence of human PPARδ (SEQ.ID.NO.:7).

FIG. 10B–C shows the nucleotide sequence of a cDNA encoding human PPARδ (SEQ.ID.NO.:8). The open reading frame is at positions 338–1663.

DETAILED DESCRIPTION OF THE INVENTION

Figure 1:
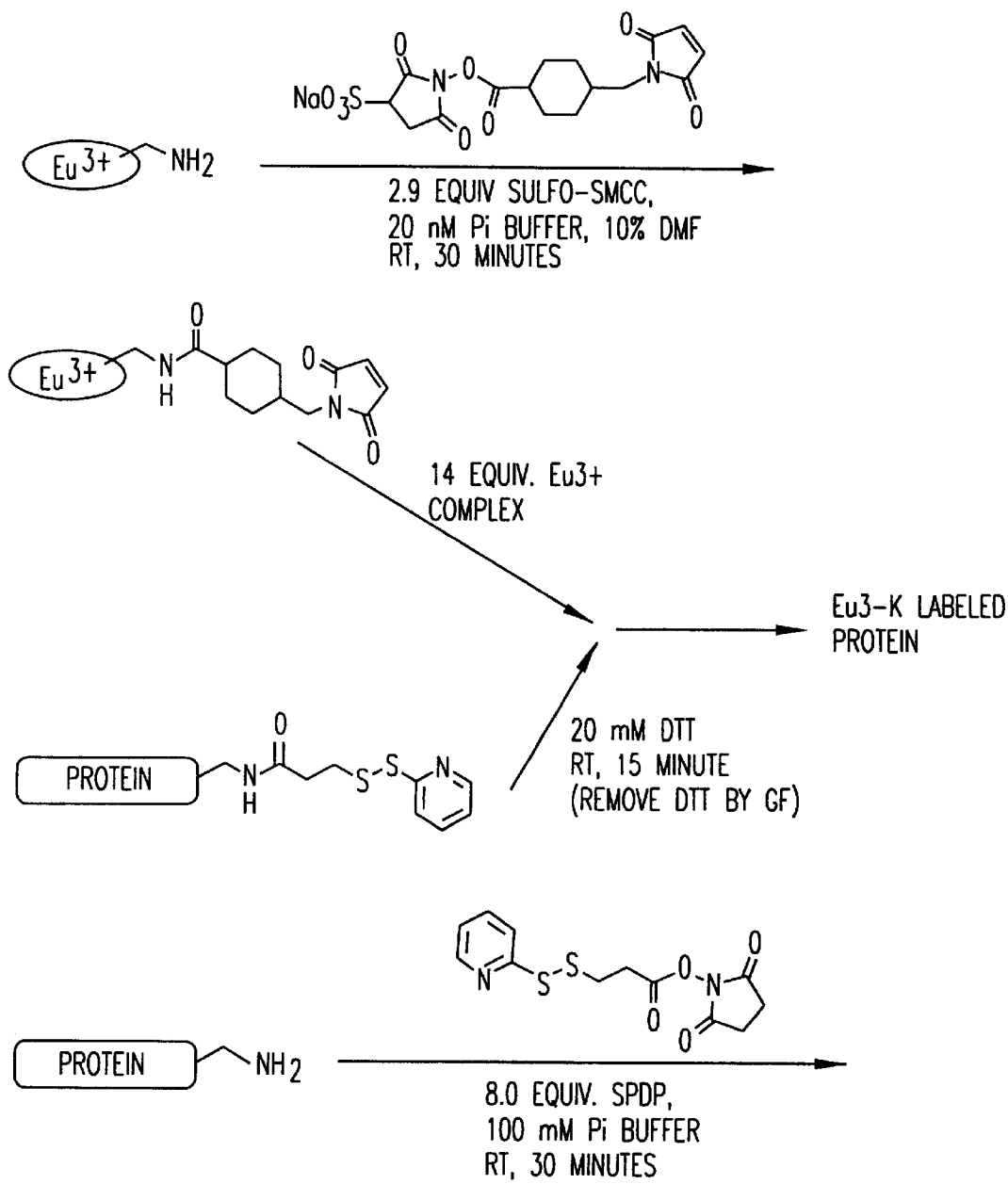
FIG. 1 illustrates a method of fluorescently labelling a protein or polypeptide with Europium cryptate (Eu3+K).

For the purposes of this invention:

an "agonist" is a substance that binds to nuclear receptors in such a way that a specific binding interaction between the nuclear receptor and CBP or other nuclear receptor co-activator can occur.

an "antagonist" is a substance that is capable of preventing or disrupting the agonist-induced specific binding interaction between a nuclear receptor and CBP, p300, or another nuclear receptor co-activator.

a "ligand" of a nuclear receptor is an agonist or an antagonist of the nuclear receptor.

a "specific binding interaction," "specific binding," and the like, refers to binding between a nuclear receptor and CBP, p300, or other nuclear receptor co-activator which results in the occurrence of fluorescence resonance energy transfer between a fluorescent reagent bound to the nuclear receptor and a fluorescent reagent bound to CBP, p300, or other nuclear receptor co-activator.

With respect to CBP, p300, or other nuclear receptor co-activators, a "binding portion" is that portion of CBP, p300, or other nuclear receptor co-activators that is sufficient for specific binding interactions with nuclear receptors.

With respect to nuclear receptors, a "ligand binding domain" is that portion of a nuclear receptor that is sufficient to bind an agonist or antagonist of the nuclear receptor.

The present invention provides a high throughput, time and labor-saving, non-radioactive, inexpensive, and very reliable assay for the identification and characterization of both agonists and antagonists of nuclear receptors. In a general embodiment, the present invention provides methods of identifying agonists and antagonists for any nuclear receptor for which CBP, p300, or another nuclear receptor binding protein is a co-activator. Such agonists and antagonists are identified by virtue of their ability to induce or prevent binding between the ligand binding domain of a nuclear receptor and CBP, p300, or other nuclear receptor co-activator. The interaction between the nuclear receptor and CBP, p300, or other nuclear receptor co-activator is monitored by observing the occurrence of fluorescence resonance energy transfer (FRET) between two fluorescent reagents. One fluorescent reagent is bound to the nuclear receptor; the other fluorescent reagent is bound to CBP, p300, or other nuclear receptor co-activator. The binding of fluorescent reagent to nuclear receptor, CBP, p300, or other nuclear receptor co-activator can be by a covalent linkage or a non-covalent linkage.

The present invention makes use of fluorescence resonance energy transfer (FRET). FRET is a process in which energy is transferred from an excited donor fluorescent reagent to an acceptor fluorescent reagent by means of intermolecular long-range dipole-dipole coupling. FRET typically occurs over distances of about 10 è to 100 è and requires that the emission spectrum of the donor reagent and the absorbance spectrum of the acceptor reagent overlap adequately and that the quantum yield of the donor and the absorption coefficient of the acceptor be sufficiently high. In addition, the transition dipoles of the donor and acceptor fluorescent reagents must be properly oriented relative to one another. For a review of FRET and its applications to biological systems, see Clegg, 1995, Current Opinions in Biotechnology 6:103–110.

The present invention makes use of a nuclear receptor or ligand binding domain thereof labeled with a first fluorescent reagent and CBP, p300, or other nuclear receptor co-activator, or a binding portion thereof, labeled with a second fluorescent reagent. The second fluorescent reagent comprises a fluorophore capable of undergoing energy transfer by either (a) donating excited state energy to the first fluorescent reagent, or (b) accepting excited state energy from the first fluorescent reagent. In other words, according to the present invention, either the first or the second fluorescent reagents can be the donor or the acceptor during FRET.

The first and second fluorescent reagents are spectroscopically complementary to each other. This means that their spectral characteristics are such that excited state energy transfer can occur between them. FRET is highly sensitive to the distance between the first and second fluorescent reagents. For example, FRET varies inversely with the sixth power of the distance between the first and second fluorescent reagents. In the absence of agonist, the first fluorescent reagent, bound to the nuclear receptor or ligand binding domain thereof, will not be near the second fluorescent reagent, bound to CBP, p300, or other nuclear receptor co-activator, or binding portion thereof. Thus, no FRET, or very little FRET, will be observed. In the presence of agonist, however, interaction between the nuclear receptor and CBP, p300, or other nuclear receptor co-activator will occur, thus bringing close together the first and the second fluorescent reagents, allowing FRET to occur and be observed.

Accordingly, the present invention provides a method of identifying an agonist of a nuclear receptor that comprises providing:

(a) a nuclear receptor or ligand binding domain thereof labeled with a first fluorescent reagent;

(b) CBP, p300, or other nuclear receptor co-activator, or a binding portion thereof, labeled with a second fluorescent reagent; and (c) a substance suspected of being an agonist of the nuclear receptor;

under conditions such that, if the substance is an agonist of the nuclear receptor, binding between the nuclear receptor or ligand binding domain thereof and CBP, p300, or other nuclear receptor co-activator, or a binding portion thereof, will occur; and (d) measuring fluorescence resonance energy transfer (FRET) between the first and second fluorescent reagents;

where the occurrence of FRET indicates that the substance is an agonist of the nuclear receptor.

In particular embodiments, the nuclear receptor is selected from the group consisting of steroid receptors, thyroid hormone receptors, retinoic acid receptors, peroxisome proliferator-activated receptors, retinoid X receptors, glucocorticoid receptors, vitamin D receptors, and "orphan nuclear receptors" such as LXR, FXR, etc.

In a particular embodiment, the nuclear receptor or ligand binding domain thereof is a full-length nuclear receptor. In another embodiment, the nuclear receptor or ligand binding domain thereof is a ligand binding domain of a nuclear receptor. In another embodiment, the nuclear receptor or ligand binding domain thereof comprises an AF-2 site of a nuclear receptor.

In a particular embodiment, the nuclear receptor or ligand binding domain thereof is a full-length PPAR. In another embodiment, the nuclear receptor or ligand binding domain thereof is the ligand binding domain of a PPAR. In a further embodiment, the PPAR is selected from the group consisting of PPARα, PPARγ1, PPARγ2, and PPARδ. In a further embodiment, the ligand binding domain of the PPAR contains amino acid residues 176–478 of human PPARγ1.

In a particular embodiment, the nuclear receptor or ligand binding domain thereof contains amino acids 143–462 of human RARα. In another embodiment, the nuclear receptor or ligand binding domain thereof contains amino acids 122–410 of rat $T_3R\alpha1$. In another embodiment, the nuclear receptor or ligand binding domain thereof contains amino acids 227–463 of mouse RXRγ. In another embodiment, the nuclear receptor or ligand binding domain thereof contains amino acids 251–595 of human ER.

In a particluar embodiment, the above-described methods utilize full-length CBP, either mouse or human. In other embodiments, the methods utilize amino acid residues 1–113 of human CBP. In another embodiment, the methods utilize amino acid residues 1–453 of human CBP.

The conditions under which the methods described above are carried out are conditions that are typically used in the art for the study of protein-protein interactions: e.g., physiological pH; salt conditions such as those represented by such commonly used buffers as PBS; a temperature of about 4° C. to about 55° C. The presence of commonly used non-ionic detergents, e.g., NP-40®, sarcosyl, Triton X-100®, is optional. When europium cryptates are used as fluorescent reagents, reactions should contain KF at a concentration of at least 200 mM.

Heery et al., 1997, Nature 387:733–736 showed that interactions between nuclear receptors and a variety of nuclear receptor co-activators are mediated by a short amino acid sequence in the nuclear receptor co-activators having the amino acid sequence LXXLL, where L is leucine and X represents any amino acid. Accordingly, the present invention can be practiced with a binding portion of a nuclear receptor co-activator, provided that the binding portion contains the amino acid sequence LXXLL. Therefore, the present invention includes a method of identifying an agonist of a nuclear receptor that comprises providing:

(a) a nuclear receptor or ligand binding domain thereof labeled with a first fluorescent reagent;

(b) a binding portion of a nuclear receptor co-activator, where the binding portion contains the amino acid sequence LXXLL, and where the binding portion is labeled with a second fluorescent reagent; and (c) a substance suspected of being an agonist of the nuclear receptor;

under conditions such that, if the substance is an agonist of the nuclear receptor, binding between the nuclear receptor or ligand binding domain thereof and the binding portion of the nuclear receptor co-activator will take place; and (d) measuring fluorescence resonance energy transfer (FRET) between the first and second fluorescent reagents;

where the occurrence of FRET indicates that the substance is an agonist of the nuclear receptor.

In a particular embodiment, the nuclear receptor co-activator is selected from the group consisting of: human RIP-140, human SRC-1, mouse TIF-2, human or mouse CBP, human or mouse p300, mouse TIF-1, and human TRIP proteins.

In a particular embodiment, the nuclear receptor co-activator is human RIP-140 and the binding portion includes a contiguous stretch of amino acids of human RIP-140 selected from the group consisting of: positions 20–29, 132–139, 184–192, 266–273, 379–387, 496–506, 712–719, 818–825, 935–944, and 935–942.

In another embodiment, the nuclear receptor co-activator is human SRC-1 and the binding portion includes a contiguous stretch of amino acids of human SRC-1 selected from the group consisting of: positions 45–53, 632640, 689–696, 748–755, and 1434–1441.

In another embodiment, the nuclear receptor co-activator is mouse TIF-2 and the binding portion includes a contiguous stretch of amino acids of mouse TIF-2 selected from the group consisting of: positions 640–650, 689–699, and 744–754.

In another embodiment, the nuclear receptor co-activator is human or mouse CBP and the binding portion includes a contiguous stretch of amino acids of human or mouse CBP selected from the group consisting of: positions 68–78 and 356–366.

In another embodiment, the nuclear receptor co-activator is human or mouse p300 and the binding portion includes a contiguous stretch of amino acids of human or mouse p300 selected from the group consisting of: positions 80–90 and 341–351.

In another embodiment, the nuclear receptor co-activator is mouse TIF-1 and the binding portion includes a contiguous stretch of amino acids of mouse TIF-1 containing positions 722–732.

In another embodiment, the nuclear receptor co-activator is human TRIP2 and the binding portion includes a contiguous stretch of amino acids of human TRIP2 containing positions 23–33.

In another embodiment, the nuclear receptor co-activator is human TRIP3 and the binding portion includes a contiguous stretch of amino acids of human TRIP3 containing positions 97–107.

In another embodiment, the nuclear receptor co-activator is human TRIP4 and the binding portion includes a contiguous stretch of amino acids of human TRIP4 containing positions 36–46.

In another embodiment, the nuclear receptor co-activator is human TRIP5 and the binding portion includes a contiguous stretch of amino acids of human TRIPS containing positions 26–36.

In another embodiment, the nuclear receptor co-activator is human TRIP8 and the binding portion includes a contiguous stretch of amino acids of human TRIP8 containing positions 36–46.

In another embodiment, the nuclear receptor co-activator is human TRIP9 and the binding portion includes a contiguous stretch of amino acids of human TRIP9 selected from the group consisting of: positions 73–83, 256–266 and 288–298.

For amino acid sequences of nuclear receptor co-activators, see Yao et al., 1996, Proc. Natl. Acad. Sci.

USA 93:10626–10631 (SRC-1); O§ate et al., 1995, Science 270:1354–1357 (SRC-1); Cavaillès et al., 1995, EMBO J. 14:3741–3751 (RIP-140); Voegel et al., 1996, EMBO J. 15:101–108 (TIF-2); Kwok et al., 1994, Nature 370:223–226 (CBP); Arias et al., 1994, Nature 370:226–229 (CBP); Eckner et al., 1994, Genes Dev. 8:869–884 (p300); Le Douarin et al., 1995, EMBO J. 14:2020–2033 (TIF-1); Lee et al., 1995, Nature 374:91–94 (TRIP proteins).

The particular embodiments of the present invention described above are all particular embodiments of a more general method that is also part of the present invention. That general method is a method of identifying an agonist of a nuclear receptor that comprises providing:

(a) a nuclear receptor or ligand binding domain thereof labeled with a first fluorescent reagent;

(b) a polypeptide containing the amino acid sequence LXXLL where the polypeptide is labeled with a second fluorescent reagent; and (c) a substance suspected of being an agonist of the nuclear receptor;

under conditions such that, if the substance is an agonist of the nuclear receptor, binding between the nuclear receptor or ligand binding domain thereof and the polypeptide will take place; and (d) measuring fluorescence resonance energy transfer (FRET) between the first and second fluorescent reagents;

where the occurrence of FRET indicates that the substance is an agonist of the nuclear receptor.

In a particular embodiment, the amino acid sequence LXXLL is present in an α helical portion of the polypeptide. In another embodiment, the amino acid sequence LXXLL is present in an α helical portion of the polypeptide and the leucines form a hydrophobic face.

The present invention provides methods for identifying antagonists of a nuclear receptor. Such methods are based on the ability of the antagonist to prevent the occurrence of agonist-induced binding between a nuclear receptor and CBP, p300, or other nuclear receptor co-activator, or to disrupt such binding after it has occurred. Thus, the present invention provides a method for identifying antagonists of nuclear receptors that comprises providing:

(a) a nuclear receptor or ligand binding domain thereof labeled with a first fluorescent reagent;

(b) CBP, p300, or other nuclear receptor co-activator, or a binding portion thereof, labeled with a second fluorescent reagent;

(c) an agonist of the nuclear receptor; and (d) a substance suspected of being an antagonist of the nuclear receptor;

under conditions such that, in the absence of the substance, binding between the nuclear receptor or ligand binding domain thereof and CBP, p300, or other nuclear receptor co-activator, or a binding portion thereof will occur; and (e) measuring fluorescence resonance energy transfer (FRET) between the first and second fluorescent reagents when the substance is present and measuring FRET between the first and second fluorescent reagents when the substance is absent;

where the a decrease in FRET when the substance is present indicates that the substance is an antagonist of the nuclear receptor.

In particular embodiments, the nuclear receptor is selected from the group consisting of steroid receptors, thyroid hormone receptors, retinoic acid receptors, peroxisome proliferator-activated receptors, retinoid X receptors, glucocorticoid receptors, vitamin D receptors, and "orphan nuclear receptors" such as LXR, FXR, etc.

In a particular embodiment, the nuclear receptor or ligand binding domain thereof is a full-length nuclear receptor. In another embodiment, the nuclear receptor or ligand binding domain thereof is a ligand binding domain of a nuclear receptor. In another embodiment, the nuclear receptor or ligand binding domain thereof is an AF-2 site of a nuclear receptor.

In a particular embodiment, the nuclear receptor or ligand binding domain thereof is a full-length PPAR. In another embodiment, the nuclear receptor or ligand binding domain thereof is the ligand binding domain of a PPAR. In a further embodiment, the PPAR is selected from the group consisting of PPARα, PPARγ, and PPARδ. In a further embodiment, the ligand binding domain of the PPAR contains amino acid residues 176–478 of human PPARγ1.

In a particular embodiment, the nuclear receptor or ligand binding domain thereof contains amino acids 143–462 of human RARα. In another embodiment, the nuclear receptor or ligand binding domain thereof contains amino acids 122–410 of rat $T_3R\alpha1$. In another embodiment, the nuclear receptor or ligand binding domain thereof contains amino acids 227–463 of mouse RXRγ. In another embodiment, the nuclear receptor or ligand binding domain thereof contains amino acids 251–595 of human ER. 5 In a particular embodiment, the above-described methods utilize full-length CBP, either mouse or human. In other embodiments, the methods utilize amino acid residues 1–113 of human CBP. In another embodiment, the methods utilize amino acid residues 1–453 of human CBP.

The conditions under which the methods described above are carried out are conditions that are typically used in the art for the study of protein-protein interactions: e.g., physiological pH; salt conditions such as those represented by such commonly used buffers as PBS; a temperature of about 40° C. to about 55° C. The presence of commonly used non-ionic detergents, e.g., NP-40®, sarcosyl, Triton X-100®, is optional. When europium cryptates are used as fluorescent reagents, reactions should contain KF at a concentration of at least 200 mM.

In principle, one could measure FRET by monitoring either (a) a decrease in the emission of the donor fluorescent reagent following stimulation at the donor's absorption wavelength and/or (b) an increase in the emission of the acceptor reagent following stimulation at the donor's absorption wavelength. In practice, FRET is most effectively measured by emission rationing. Emission rationing monitors the change in the ratio of emission by the acceptor over emission by the donor. An increase in this ratio signifies that energy is being transferred from donor to acceptor and thus that FRET is occurring. Emission rationing can be measured by employing a laser-scanning confocal microscope. Emission ratioing is preferably done by splitting the emitted light from a sample with a dichroic mirror and measuring two wavelength bands (corresponding to the donor and the acceptor emission wavelengths) simultaneously with two detectors. Alternatively, the emitted light can be sampled consecutively at each wavelength (by using appropriate filters) with a single detector. In any case, these and other methods of measuring FRET are well known in the art.

Although a variety of donor and acceptor fluorescent reagents can be used in the practice of the present invention, preferred embodiments of the present invention make use of cryptates of fluorescent reagents as donor reagents. Inclusion of a substrate into the intramolecular cavity of a macropolycyclic ligand results in the formation of a cryptate. The macropolycyclic ligand shields the substrate from interaction with solvent and other solute molecules. If the substrate is a fluororescent reagent, formation of a cryptate may result in markedly different spectroscopic characteristics for the reagent as compared to the spectroscopic characteristics of the free reagent.

The present invention includes the use of europium ($Eu^{III}$) or terbium ($Tb^{III}$) cryptates as donor fluorescent reagents. Such $Eu^{III}$ or $Tb^{III}$ cryptates, as well as methods for their formation, are well known in the art. For example, see Alpha et al., 1987, Angew. Chem. Int. Ed. Engl. 26:266–267; Mathis, 1995, Clin. Chem. 41:1391–1397. A europium cryptate is formed by the inclusion of a europium ion into the intramolecular cavity of a macropolycyclic ligand which contains bipyridine groups as light absorbers. When europium cryptates are present in solution together with fluoride ions, a total shielding of the europium cryptate fluorescence is occurs. The molecular structure of a europium cryptate is shown below.

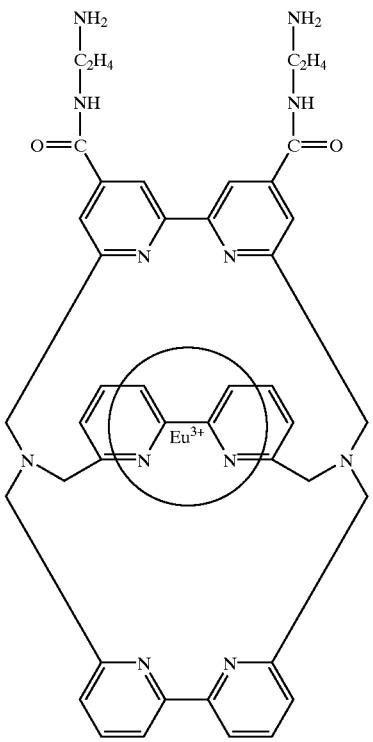

Europium cryptates can be conjugated to proteins by the use of well-known heterobifunctional reagents (see, e.g., International Patent Application WO 89/05813; Prat et al., 1991, Anal. Biochem. 195:283–289; Lopez et al., 1993, Clin. Chem. 39:196–201).

The present invention includes the use of XL665 as the acceptor fluorescent reagent. XL665 is a crosslinked derivative of allophycocyanin (APC). APC is a porphyrin containing protein which is derived from the light harvesting system of algae (Kronick, 1986, M. Immunol. Meth. 92:1–13). XL665 has an absorption maximum at ≈620 nm and an emission maximum at 665 nm. In some embodiments of the invention, XL665 is labeled with streptavidin in order to effect the binding of the streptavidin-lableled XL665 to a biotin-labeled substance, e.g., CBP or the ligand binding domain of a nuclear receptor. Streptavidin labeling of XL655 and biotin labeling of CBP, or the ligand binding domain of a nuclear receptor, can be performed by well known methods.

In a preferred embodiment of the invention, XL665 as the acceptor fluorescent reagent is combined with Europium cryptate (Eu3+K) as the donor fluorescent reagent. Europium cryptate (Eu3+K) has a large Stokes shift, absorbing light at 337 nm and emitting at 620 nm. Thus, the emission maximum of Europium cryptate (Eu3+K) overlaps the absorption maximum of XL665. Europium cryptate (Eu3+K) has a large temporal shift; the time between absorption and emission of a photon is about 1 millisecond. This is advantageous because most background fluorescence signals in biological samples are short-lived. Thus the use of a fluorescent reagent such as europium cryptate, with a long fluorescent lifetime, permits time-resolved detection resulting in the reduction of background interference.

The spectral and temporal properties of europium cryptate (Eu3+K) result in essentially no fluorescence background and thus assays using this fluorescent reagent can be carried out in a "mix and read" mode, greatly facilitating its use as a high throughput screening tool. For the embodiment using Europium cryptate (Eu3+K) and XL665, the measuring instrument irradiates the sample at 337 nm and measures the fluorescence output at two wavelengths, 620 nm (B counts, europium fluorescence) and 665 nm (A counts, XL665 fluorescence).

The extent of flurorescent resonance energy transfer is measured as the ratio between these two values. Typically this ratio is multiplied by 10,000 to give whole numbers.

Other FRET donor-acceptor pairs are suitable for the practice of the present invention. For example, the following donor-acceptor pairs can be used: dansyl/fluorescein; fluorescein/rhodamine; tryptophan/aminocoumarin.

The present invention provides a nuclear receptor or ligand binding domain thereof labeled with a fluorescent reagent for use in the above-described methods of identifying agonists and antagonists of nuclear receptors. The present invention also provides CBP, p300, or other nuclear receptor co-activator, or a binding portion thereof, labeled with a fluorescent reagent.

In a particular embodiment, the nuclear receptor or ligand binding domain thereof is selected from the group consisting of PPARα, PPARγ, PPARδ, a ligand binding domain of PPARα, PPARγ, or PPARδ, and amino acid residues 176–478 of human PPARγ1 and the fluorescent reagent is selected from the group consisting of XL665 and Europium cryptate (Eu3+K).

In a particular embodiment, CBP, p300, or other nuclear receptor co-activator is labeled with a fluorescent reagent selected from the group consisting of XL665 and Europium cryptate (Eu3+K).

The following non-limiting examples are presented to better illustrate the invention.

EXAMPLE 1

Cloning expression and Purification of Human CBP and PPAR Proteins

To test whether human CBP can interact with PPARs in an agonist-dependent manner, we cloned the human cDNA fragments encoding the $NH_2$-terminal 1–113 amino acids (hCBP1–113) and 1–453 amino acids (hCBP1–453) of human CBP by the polymerase chain reaction (PCR). The DNA and amino acid sequences of human CBP are disclosed in Borrow et al., 1996, Nature Genet. 14:33–41 and in GenBank, accession no. U47741.

The primers used for hCBP1-113 were:
5'-ACTCGGATCCAAGCCATGGCTGAGAACTTGCT GGACGG-3' (SEQ.ID.NO.:9) and
5'-CACAAAGCTTAGGCCATGTTAGCACTGTTCGG-3'(SEQ.ID.NO.: 10).
These primers were expected to amplify a 0.9 kb DNA fragment.

The primers for hCBP1-453 were:
5'-ACTCGGATCCAAGCCATGGCTGAGAACTTGCT GGACGG-3'(SEQ.ID.NO.:9) and
5'CTCAGTCGACTTATTGAATTCCACTAGCTGGAGA TCC-3'(SEQ.ID.NO.:11).
These primers were expected to amplify a 1.5 kb DNA fragment.

The template for the PCR reaction was a human fetal brain cDNA library (Stratagene, Catalogue #IS 937227). Of course, any human cDNA library from a tissue expressing CBP could have been used. The PCR amplified 0.9 kb and 1.5 kp DNA fragments which were digested with restriction endonucleases and ligated into pBluescript II vector. DNA sequencing analysis confirmed that the amplified fragments were identical to the corresponding published nucleic acid sequences of human CBP.

Based on the publicly available sequences for human CBP cited above, other primers could be readily identified and prepared by those skilled in the art in order to amplify and clone other portions of cDNA encoding human CBP from appropriate cDNA libraries. Once such portions of human CBP are produced, they could be used in the methods of the present invention in a manner similar to that described herein for hCBP1-113 and hCBP1-453. The amino acid sequence of human CBP is shown in FIG. 7A; the nucleic acid sequence of the cDNA encoding human CBP is shown in FIG. 7B.

To express the polypeptides encoded by the PCR fragments, vectors encoding fusion proteins of the polypeptides and glutathione S-transferase (GST) were constructed and expressed in E. coli. The PCR fragments were subcloned into the expression vector PGEX (Pharmacia Biotech) to generate pGEXhCBP1-113 and pGEXhCBP1-453. pGEX-hCBP1-113 and pGEXhCBP1-453 were transfected into the DH5α strain of E. coli (GIBCO BRL) and the bacteria hosting either pGEXhCBP1-113 or pGEXhCBP1-453 were cultured in LB medium (GIBCO BRL) to a density of $OD_{600}$=0.7–1.0 and induced for overexpression of the GST-CBP fusion proteins by addition of IPTG (isopropylthio-p-galactoside) to a final concentration of 0.2 mM. The IPTG induced cultures were further grown at room temperature for 2–5 hrs. The cells were harvested by centrifugation for 10 min at 5000 g. The cell pellet was used for GST-CBP fusion protein purification by following the procedure from Pharmacia Biotech using Glutathione Sepharose beads. hCBP1-113 and hCBP1-453 proteins were generated by cleaving the corresponding GST fusion proteins with thrombin. SDS-polyacrylamide gel electrophoresis analysis showed that the preparation from pGEXhCBP1-113 gave two polypeptide bands, with apparent molecular weight of 12 kd and 10 kd. The 12 kd band is the expected size of hCBP1-113 and the 10 kd band is most likely a premature translational termination product. The preparation from pGEXhCBP1-450 gave a single band with the expected size, 50 kd.

cDNAs encoding full-length PPARα and PPARγ1 were subcloned into pGEX vectors for the production of GST-PPARα and GST-PPARγ1 fusion proteins in E. coli. PPARγ1 was cloned from a human fat cell cDNA library (see Elbrecht et al., 1996, Biochem. Biophys. Res. Comm. 224:431–437). A cDNA encoding the human PPARγ1 ligand binding domain (PPARγ1LBD; amino acids 176–478 of PPARγ1) was subcloned from a modified pSG5 vector as a Xho I (site located in the N-terminus of the LBD)/Xba I (site located in the pSG5 vector) fragment. The Xba I site was blunt-ended with T4 DNA polymerase. The 1.1 kb fragment containing the LBD was purified from an agarose gel and ligated into pGEX-KG (see Guan & Dixon, 1991, Anal. Biochem. 192:262–267) that had been digested with Xho I and Hind III (the Hind III site had been blunt-ended with T4 DNA polymerase). This construct was used for the production of GST-hPPARγ1LBD and hPPARγ1LBD (the ligand binding domain cleaved free of GST). The overexpression and purification of PPARα, PPARγ1, and PPARγ1LBD were as described above for CBP.

The DNA and amino acid sequences of human PPARα are disclosed in Schmidt et al., 1992, Mol. Endocrinol. 6:1634–1641 and in GenBank, accession no. L07592. See FIGS. 8A and 8B.

The DNA and amino acid sequences of human PPARγ1 are disclosed in Greene et al., 1995, Gene Expr. 4:281–299; Qi et al., 1995, Mol. Cell. Biol. 15:1817–1825; Elbrecht et al., 1996, Biochem. Biophys. Res. Comm. 224:431–437; and in GenBank, accession no. L40904. See FIGS. 9A and 9B. Human PPARγ2 contains the same amino acid sequence as human PPARγ1 except for an amino terminal addition of 24 amino acids (see Elbrecht et al., 1996, Biochem. Biophys. Res. Comm. 224:431–437). Thus, the amino acid sequence of the ligand binding domain of human PPARγ2 is the same as the amino acid sequence of the ligand binding domain of human PPARγ1, although the numbering of the amino acids differs (176–478 for human PPARγ1 and 200–502 for human PPARγ2).

The DNA and amino acid sequences of human PPARδ5 are disclosed in Sher et al., 1993, Biochemistry 32:5598–5604 and in GenBank, accession no. L02932. See FIGS. 10A-C.

EXAMPLE 2

Interaction Between PPARs and hCBP Fragments

Experiments were first conducted using hCBP1-113 and hPPARγ1LBD. Purified hPPARγ1LBD was biotinylated with Sulfo-NHS-LC-Biotin (PIERCE) to a biotin:hPPARγ1LBD ratio of 3:1 according to the procedure provided by PIERCE. Purified hCBP1-113 was directly labeled with europium cryptate (Eu3+K) by the method illustrated in FIG. 1. Biotin-labeled hPPARγ1LBD, Eu3+K-labeled hCBP1-113, and streptavidin-labeled XL665 (SA-XL665; from PACKARD) were incubated together in the presence or absence of 1 μM of known PPARγ agonist (BRIA9653 or AD5075).

Figure 2:
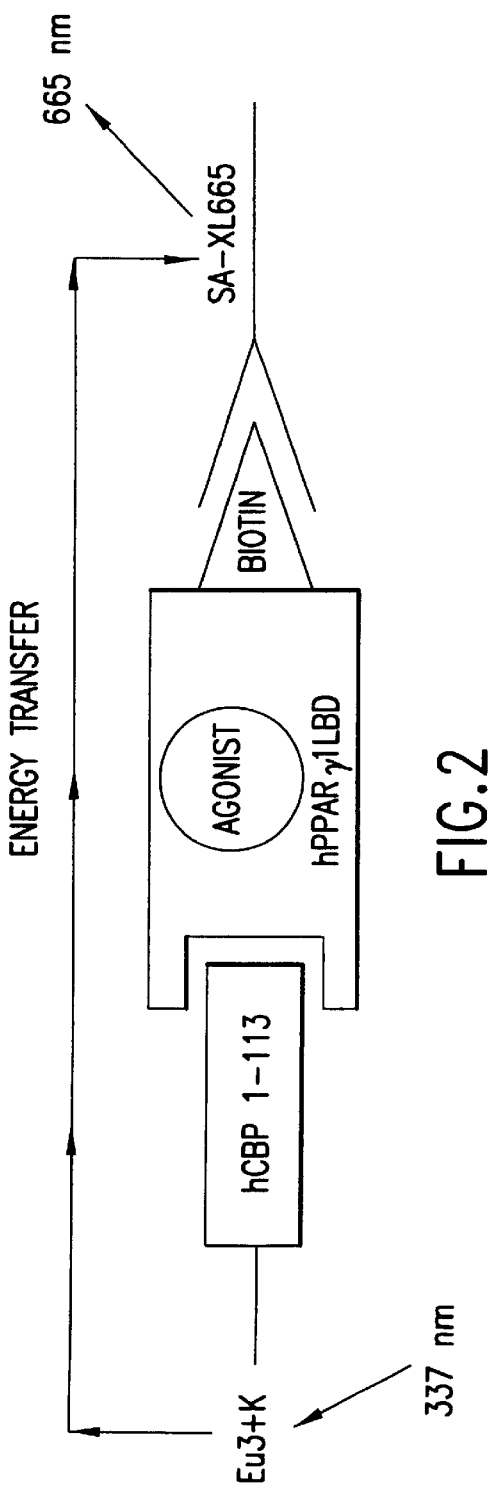
FIG. 2 illustrates the format for experiments 1 and 2 of Table 1.

Thus, this experimental format made use of the fluorescent reagent pair europium cryptate (Eu3+K), which acted as donor, and XL665, which acted as acceptor. hCBP1-113 was directly labeled with europium cryptate (Eu3+K); hPPARγ12LBD was indirectly labeled with XL665 by means of a biotin-streptavidin link. The emission maximum of europium cryptate (Eu3+K) overlaps with the absorption maximum of XL665. Therefore, when europium cryptate (Eu3+K) and XL665 are in close proximity, and the sample is illuminated with light at 337 nm (the absorption maximum of europium cryptate (Eu3+K)), FRET can occur between europium cryptate (Eu3+K) and XL665. This FRET manifests itself as increased emission at 665 nm by XL665. FIG. 2 shows a schematic of the format used in this experiment (experiment 1 of Table 1). When agonist is bound to hPPARγ1LBD, a specific interaction occurs between hPPARγ1LBD and hCBP1–113, thus bringing europium cryptate (Eu3+K) and XL665 into close enough proximity for FRET to occur. In the absence of agonist, no interaction occurs between hPPARγ1LBD and hCBP1–113 and thus europium cryptate (Eu3+K) and XL665 are not brought into close proximity and no FRET occurs. When FRET occurs, the amount of light given off by the sample at the emission maximum of XL665 (665 nm) is increased relative to the amount of light given off by the sample at the emission maximum of europium cryptate (Eu3+K) (620 nm). Therefore, measuring the ratio of emission at 665 nm to 620 nm in the presence and the absence of a substance suspected of being an agonist allows for the determination of whether that substance actually is an agonist. If the substance is an agonist, an increase in the ratio of emission at 665 nm to 620 nm in the presence of the substance will be observed.

Reactions were carried out in microtiter plates. Reaction conditions were: appropriate volume (total 250 μl) of the reaction buffer (either PBS or HEPES, see below, containing 500 mM KF, 0.1% bovine serum albumin, BSA) was added to each well, followed by addition of ligands (BRL49653 or AD5075 at a final concentration of 1 μM and 0.1% dimethylsulfoxide (DMSO) or vehicle control (0.1% DMSO), Eu3+K labeled hCBP (100 nM), biotin-hPPARγ1LBD (100 nM), and streptavidin-labeled XL665 (100 nM) to appropriate wells. After mixing, 200 μl of reaction mixture was transferred to a new well. The plate was either directly measured for fluorescence resonance energy transfer (FRET) or covered with sealing tape (PACKARD) to avoid evaporation and incubated at room temperature for up to 24 hrs before measuring FRET.

The results of this experiment and others described below yielded ratio values as follows:

TABLE 1

| Experiment | Buffer | Emission ratio with AD5075 | Emission ratio with vehicle |
|---|---|---|---|
| 1 | PBS | 1134 | 1074 |
| 2 | HEPES + 0.05% NP40 | 967 | 617 |
| 3 | HEPES + 0.05% NP40 | 1078 | 536 |
| 4 | HEPES + 0.05% CHAPS | 1883 | 487 |

Experiment 1 of Table 1 was carried out using PBS (137 mM NaCl, 2.7 mM KCl, 4.3 mM $Na_2HPO_4$, 1.4 mM $KH_2PO4$, pH 7.4). The greater emission ratio observed in the presence of AD5075 demonstrated that a specific interaction between hCBP1–113 and hPPARγ1LBD occurred in the presence of the agonist AD5075. Although it was clear that FRET was occurring, the signal-noise ratio was small. In experiment 2 of Table 1, HEPES buffer (N-2-hydroxyethylpiperazine-N'-2-ethane sulfonic acid, 100 mM, pH 7.0) containing 0.05% NP40 (Nonidet P-40) was used instead of PBS and an improved signal-noise ratio was obtained.

Figure 3:
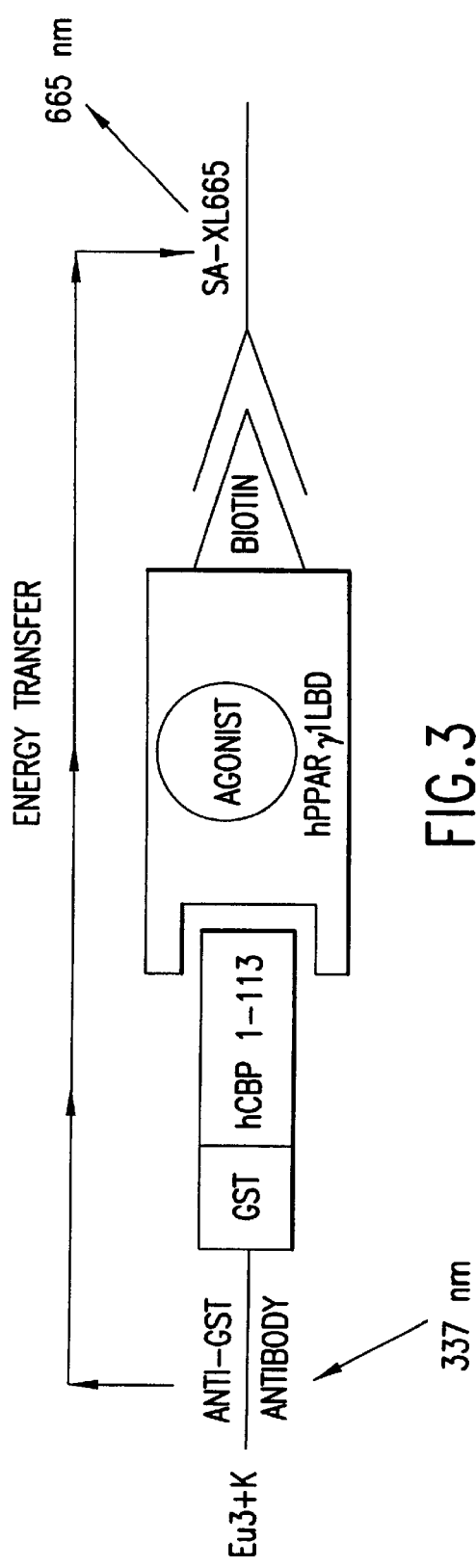
FIG. 3 illustrates the format for experiment 3 of Table 1.

In order to get an even better signal-noise ratio, the above-described format was modified slightly for experiment 3. In experiment 3, SA-XL665 (500 nM), biotin-labeled hPPARγ1LBD (100 nM), GST-hCBP1–113, and Eu3+K labeled anti-GST antibody (2.5 μl) were incubated in the presence or absence of AD5075 (1 μM) in HEPES buffer containing 0.05% NP40. A two-fold signal- noise ratio was obtained. FIG. 3 shows a schematic of the format used in experiment 3.

The anti-GST antibody was a goat antibody to GST from Pharmacia (catalogue number 27–4577–01) that was labeled with Eu3+K according to the procedure summarized below.

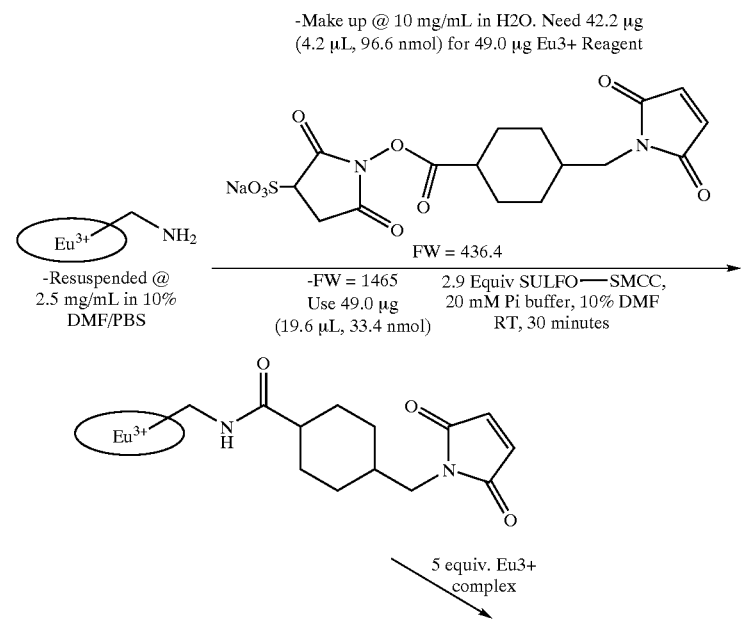

-continued

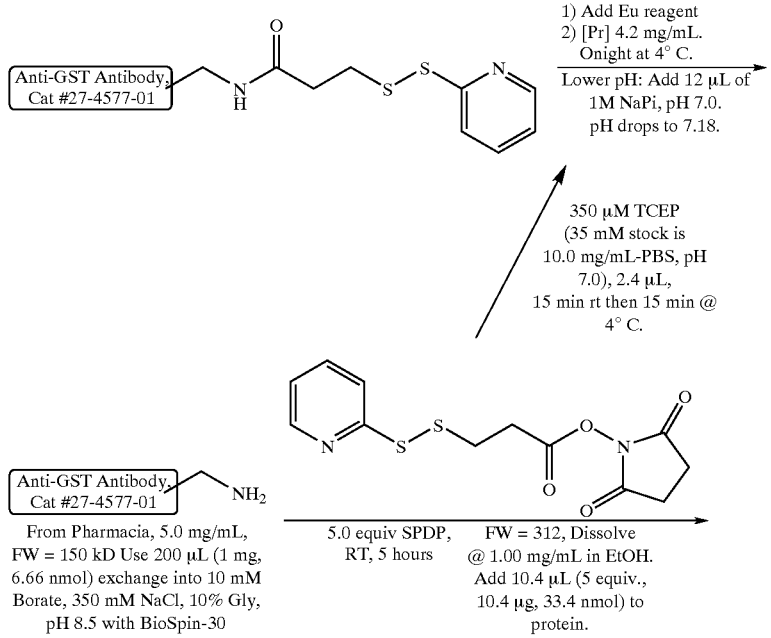

Figure 4:
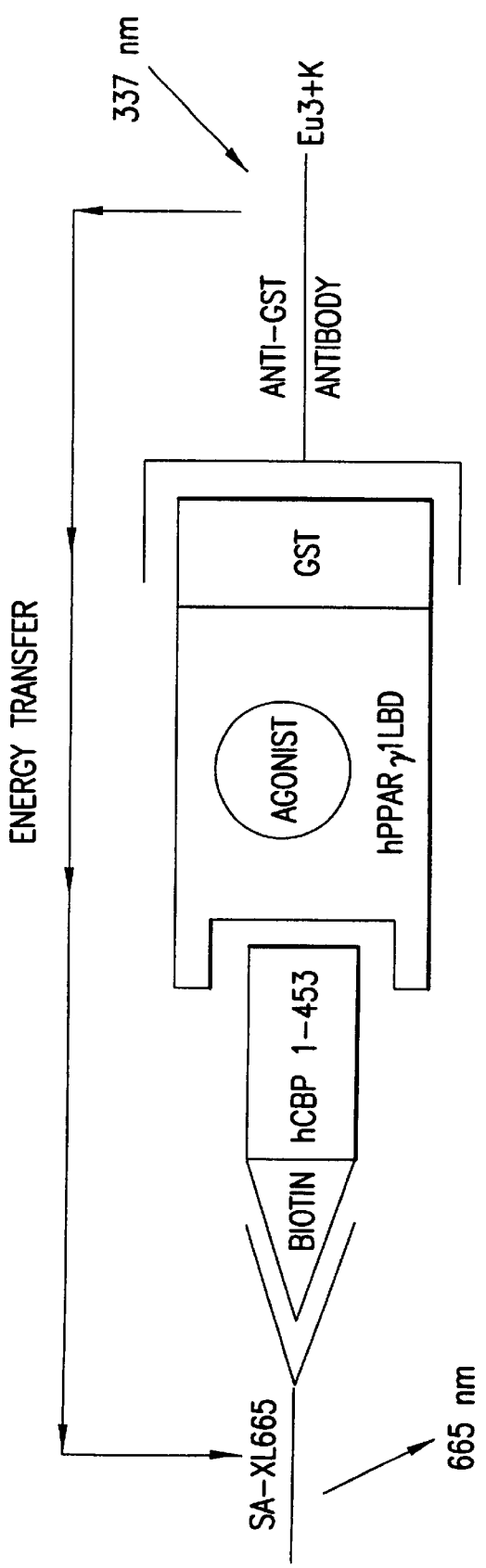
FIG. 4 illustrates the format for experiment 4 of Table 1.

To further improve the signal to noise ratio, a series of experiments were conducted. Experiment 4 of Table 1 exemplifies 5 results obtained from those efforts. cDNA encoding a longer fragment of hCBP was cloned and expressed to get hCBP1–453. hCBP1–453 was biotinylated. Biotin-labeled hCBP1–453 (25 nM), SA-XL665 (100 nM), GST-hPPARγ1LBD (1 nM), and Eu3+K-labeled anti-GST antibody (2 nM) were mixed together in the presence or absence of 1 μM AD5075. The detergent was changed from 0.05% NP40 to 0.5% CHAPS (3-{[3-cholamidopropyl] dimethyl-ammoniol}-1-propanesulfonate). A three- to four-fold signal-noise ratio was obtained. FIG. 4 shows the strategy used for experiment 4 and similar experiments.

Figure 5:
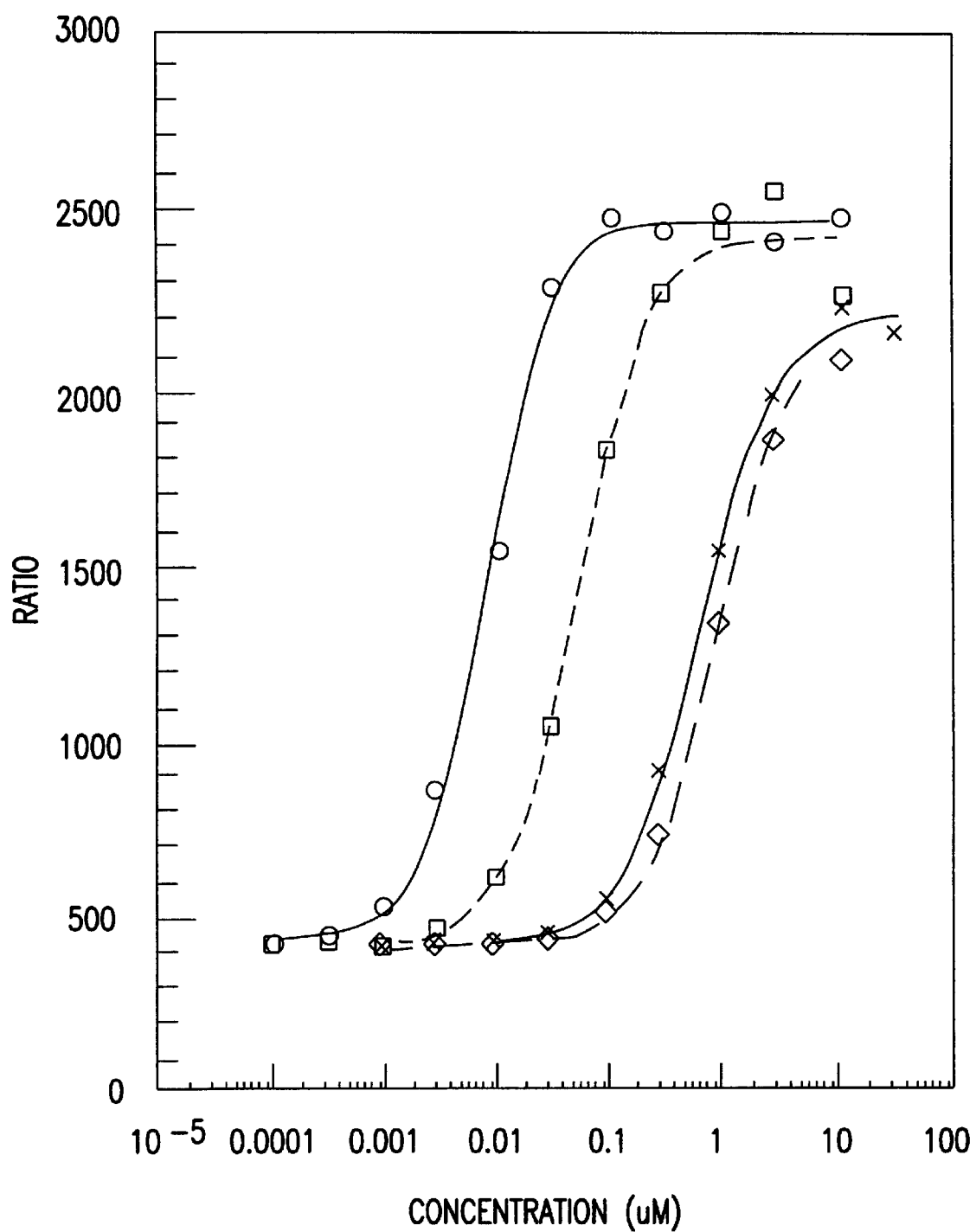
FIG. 5 shows the results of studies using the methods of the present invention with four known PPARγ agonists. --○--=AD5075; --□--=Pioglitazone; --X--=Troglitazone; --◇--=BRL49653.

The correlation between results from the above-described assays and previously reported results from in vitro binding and transcriptional activation assays of selected antidiabetic insulin sensitizers that are known to be PPARγagonists (Elbrecht et al., 1996, Biochem Biophys Res Comm 224:431–437) was analyzed by titrating those known PPARγ agonists in the assays described above and comparing $EC_{50}$s so obtained with previously described values for potency in binding or transcriptional activation assays for the known agonists. The results are shown in FIG. 5. From FIG. 5, the following $EC_{50}$s can be derived:

AD5075=8 nM
BRIA9653=53 nM
Troglitazone=646 nM
Pioglitazone=890 nM.

These $EC_{50}$s generated in the above-described assays are in close agreement with those generated by in vitro binding and transcriptional activation studies (Elbrecht et al., 1996, Biochem Biophys Res Comm 224:431437).

Figure 6:
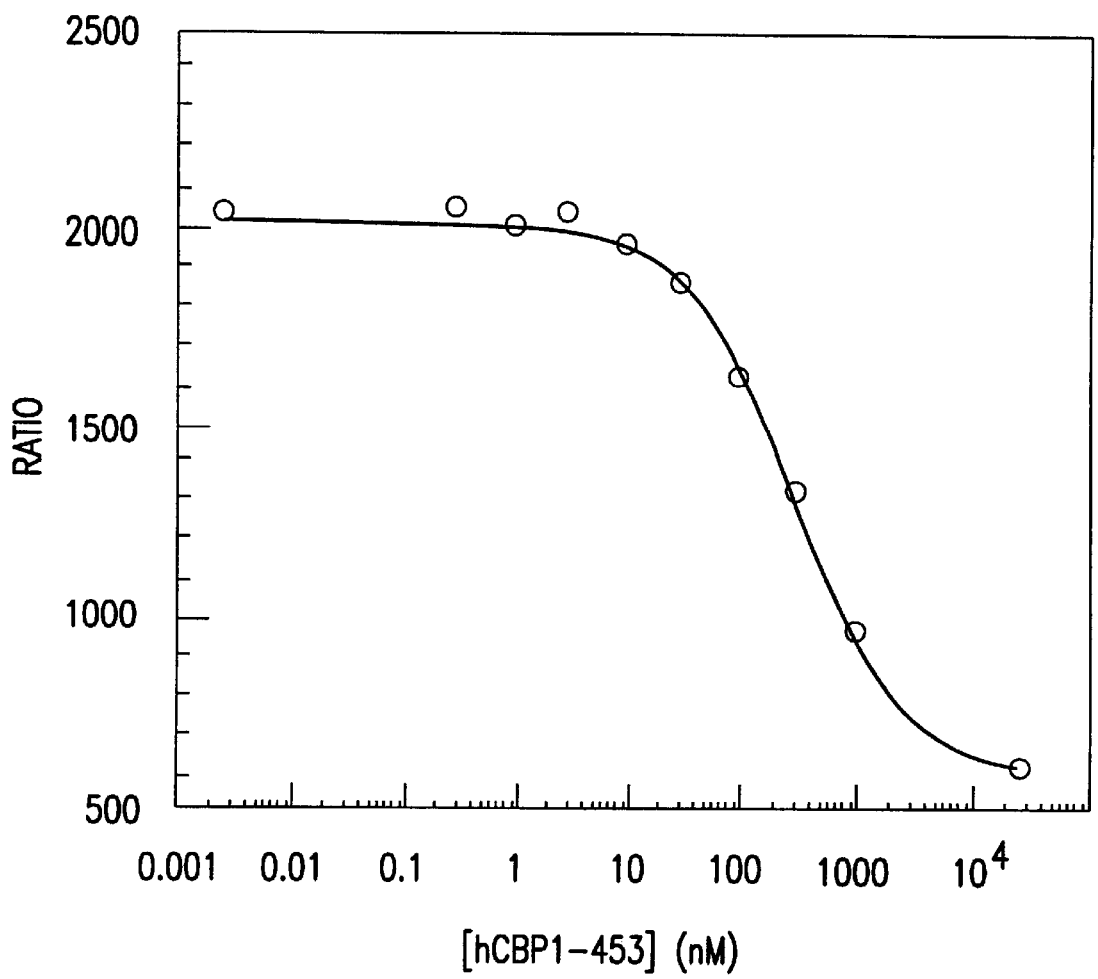
FIG. 6 shows a measurement of the binding constant for the interaction between hCBP and PPARγ1LBD.

The above-described assay can also be used to characterize the interaction between nuclear receptors with co-activators as, e.g., by determining the binding constant for that interaction. FIG. 6 shows an example of such an application. Saturating amounts of PPARγ agonist (10 μM BRL49653) were used. Increasing concentrations of non-biotinylated hCBP1–453 were used to titrate away biotin-hCBP-PPARγ1LBD complex and decrease the fluorescence energy transfer. A Kd of 300 nM for the interaction between hCBP1–453 and PPARγ1LBD can be derived from the results illustrated in FIG. 6 and this Kd (300 nM) is a measurement of the affinity between CBP and PPARγ.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed:

1. A method of identifying an agonist of a nuclear receptor that comprises providing:
   (a) a nuclear receptor or ligand binding domain thereof labeled with a first fluorescent reagent;
   (b) CBP, p300, or other nuclear receptor co-activator, or a binding portion thereof, labeled with a second fluorescent reagent; and
   (c) a substance suspected of being an agonist of the nuclear receptor;
      under conditions such that, if the substance is an agonist of the nuclear receptor, binding between the nuclear receptor or ligand binding domain thereof and CBP, p300, or other nuclear receptor co-activator, or a binding portion thereof, will occur; and
   (d) measuring fluorescence resonance energy transfer (FRET) between the first and second fluorescent reagents;
      where the occurrence of FRET indicates that the substance is an agonist of the nuclear receptor.

2. The method of claim 1 where the nuclear receptor or ligand binding domain thereof is selected from the group consisting of steroid receptors, thyroid hormone receptors, retinoic acid receptors, peroxisome proliferator-activated receptors, retinoid X receptors, glucocorticoid receptors, vitamin D receptors, LXR, and FXR.

3. The method of claim 1 where the nuclear receptor or ligand binding domain thereof is selected from the group consisting of a full-length nuclear receptor, a ligand binding domain of a nuclear receptor, and an AF-2 site of a nuclear receptor.

4. The method of claim 1 where the nuclear receptor or ligand binding domain thereof comprises an AF-2 site of a nuclear receptor.

5. The method of claim 1 where the nuclear receptor or ligand binding domain thereof is selected from the group consisting of a full-length PPAR, a ligand binding domain of a PPAR, and amino acid residues 176–478 of human PPARγ1.

6. The method of claim 1 where the nuclear receptor or ligand binding domain thereof is selected from the group consisting of PPARα, PPARγ1, PPARγ2, and PPARδ.

7. The method of claim 1 where the nuclear receptor or ligand binding domain thereof comprises a ligand binding domain selected from the group consisting of amino acids 143–462 of human RARα, amino acids 122–410 of rat T3Rα1, amino acids 227–463 of mouse RXRγ, and amino acids 251–595 of human ER.

8. The method of claim 1 where CBP, p300, or other nuclear receptor co-activator, or a binding portion thereof is selected from the group consisting of full-length human CBP, full-length mouse CBP, amino acid residues 1–113 of human CBP, and amino acid residues 1–453 of human CBP.

9. The method of claim 1 where the first fluorescent reagent is selected from the group consisting of XL665 and Europium cryptate (Eu3+K).

10. The method of claim 1 where the second fluorescent reagent is selected from the group consisting of XL665 and Europium cryptate (Eu3+K).

11. A method of identifying an agonist of a nuclear receptor that comprises providing:
    (a) a nuclear receptor or ligand binding domain thereof labeled with a first fluorescent reagent;
    (b) a binding portion of a nuclear receptor co-activator, where the binding portion contains the amino acid sequence LXXLL, and where the binding portion is labeled with a second fluorescent reagent; and
    (c) a substance suspected of being an agonist of the nuclear receptor;
       under conditions such that, if the substance is an agonist of the nuclear receptor, binding between the nuclear receptor or ligand binding domain thereof and the binding portion of the nuclear receptor co-activator will take place; and
    (d) measuring fluorescence resonance energy transfer (FRET) between the first and second fluorescent reagents;
       where the occurrence of FRET indicates that the substance is an agonist of the nuclear receptor.

12. The method of claim 11 where the binding portion of a nuclear receptor co-activator is selected from the group consisting of human RIP-140, human SRC-1, mouse TIF-2, human or mouse CBP, human or mouse p300, mouse TIF-1, and human TRIP proteins.

13. A method of identifying an agonist of a nuclear receptor that comprises providing:
    (a) a nuclear receptor or ligand binding domain thereof labeled with a first fluorescent reagent;
    (b) a polypeptide containing the amino acid sequence LXXLL where the polypeptide is labeled with a second fluorescent reagent; and
    (c) a substance suspected of being an agonist of the nuclear receptor;
       under conditions such that, if the substance is an agonist of the nuclear receptor, binding between the nuclear receptor or ligand binding domain thereof and the polypeptide will take place; and (d) measuring fluorescent resonance energy transfer (FRET) between the first and second fluorescent reagents;

where the occurrence of FRET indicates that the substance is an agonist of the nuclear receptor.

14. A method for identifying an antagonist of a nuclear receptor that comprises providing:

(a) a nuclear receptor or ligand binding domain thereof labeled with a first fluorescent reagent;

(b) CBP, p300, or other nuclear receptor co-activator, or a binding portion thereof, labeled with a second fluorescent reagent;

(c) an agonist of the nuclear receptor; and (d) a substance suspected of being an antagonist of the nuclear receptor;

under conditions such that, in the absence of the substance, binding between the nuclear receptor or ligand binding domain thereof and CBP, p300, or other nuclear receptor co-activator, or a binding portion thereof will occur; and (e) measuring fluorescence resonance energy transfer (FRET) between the first and second fluorescent reagents when the substance is present and measuring FRET between the first and second fluorescent reagents when the substance is absent;

where the a decrease in FRET when the substance is present indicates that the substance is an antagonist of the nuclear receptor.

15. The method of claim 14 where the nuclear receptor or ligand binding domain thereof is selected from the group consisting of steroid receptors, thyroid hormone receptors, retinoic acid receptors, peroxisome proliferator-activated receptors, retinoid X receptors, glucocorticoid receptors, vitamin D receptors, LXR, and FXR.

16. The method of claim 14 where the nuclear receptor or ligand binding domain thereof is selected from the group consisting of a full-length nuclear receptor, a ligand binding domain of a nuclear receptor, and an AF-2 site of a nuclear receptor.

17. The method of claim 14 where the nuclear receptor or ligand binding domain thereof comprises an AF-2 site of a nuclear receptor.

18. The method of claim 14 where the nuclear receptor or ligand binding domain thereof is selected from the group consisting of a full-length PPAR, a ligand binding domain of a PPAR, and amino acid residues 176–478 of human PPAR$\gamma$1.

19. The method of claim 14 where the nuclear receptor or ligand binding domain thereof is selected from the group consisting of PPAR$\alpha$, PPAR$\gamma$1, PPAR-2, and PPAR$\delta$.

20. The method of claim 14 where the nuclear receptor or ligand binding domain thereof comprises a ligand binding domain selected from the group consisting of amino acids 143–462 of human RAR$\alpha$, amino acids 122–410 of rat $T_3R\alpha1$, amino acids 227–463 of mouse RXR$\gamma$, and amino acids 251–595 of human ER.

21. The method of claim 14 where CBP, p300, or other nuclear receptor co-activator, or a binding portion thereof is selected from the group consisting of full-length CBP, amino acid residues 1–113 of human CBP, and amino acid residues 1–453 of human CBP.

22. The method of claim 14 where the first fluorescent reagent is selected from the group consisting of XL665 and Europium cryptate (Eu3+K).

23. The method of claim 14 where the second fluorescent reagent is selected from the group consisting of XL665 and Europium cryptate (Eu3+K).

* * * * *

SEQUENCE LISTING

<160> NUMBER OF SEQ ID NOS: 12

<210> SEQ ID NO 1
<211> LENGTH: 405
<212> TYPE: PRT
<213> ORGANISM: Homo sapiens

```
<400> SEQUENCE: 1

Met Ala Glu Asn Leu Leu Asp Gly Pro Pro Asn Pro Lys Arg Ala Lys
 1               5                  10                  15

Leu Ser Ser Pro Gly Phe Ser Ala Asn Asp Ser Thr Asp Phe Gly Ser
             20                  25                  30

Leu Phe Asp Leu Glu Asn Asp Leu Pro Asp Glu Leu Ile Pro Asn Gly
         35                  40                  45

Gly Glu Leu Gly Leu Leu Asn Ser Gly Asn Leu Val Pro Asp Ala Ala
     50                  55                  60

Ser Lys His Lys Gln Leu Ser Glu Leu Leu Arg Gly Gly Ser Gly Ser
 65                  70                  75                  80

Ser Ile Asn Pro Gly Ile Gly Asn Val Ser Ala Ser Ser Pro Val Gln
                 85                  90                  95

Gln Gly Leu Gly Gly Gln Ala Gln Gly Gln Pro Asn Ser Ala Asn Met
            100                 105                 110

Ala Ser Leu Ser Ala Met Gly Lys Ser Pro Leu Ser Gln Gly Asp Ser
            115                 120                 125

Ser Ala Pro Ser Leu Pro Lys Gln Ala Ala Ser Thr Ser Gly Pro Thr
        130                 135                 140

Pro Ala Ala Ser Gln Ala Leu Asn Pro Gln Ala Gln Lys Gln Val Gly
145                 150                 155                 160

Leu Ala Thr Ser Ser Pro Ala Thr Ser Gln Thr Gly Pro Gly Ile Cys
                165                 170                 175

Met Asn Ala Asn Phe Asn Gln Thr His Pro Gly Leu Leu Asn Ser Asn
            180                 185                 190

Ser Gly His Ser Leu Ile Asn Gln Ala Ser Gln Gly Gln Ala Gln Val
        195                 200                 205

Met Asn Gly Ser Leu Gly Ala Ala Gly Arg Gly Arg Gly Ala Gly Met
    210                 215                 220

Pro Tyr Pro Thr Pro Ala Met Gln Gly Ala Ser Ser Ser Val Leu Ala
225                 230                 235                 240

Glu Thr Leu Thr Gln Val Ser Pro Gln Met Thr Gly His Ala Gly Leu
                245                 250                 255

Asn Thr Ala Gln Ala Gly Gly Met Ala Lys Met Gly Ile Thr Gly Asn
            260                 265                 270

Thr Ser Pro Phe Gly Gln Pro Phe Ser Gln Ala Gly Gly Gln Pro Met
        275                 280                 285

Gly Ala Thr Gly Val Asn Pro Gln Leu Ala Ser Lys Gln Ser Met Val
    290                 295                 300

Asn Ser Leu Pro Thr Phe Pro Thr Asp Ile Lys Asn Thr Ser Val Thr
305                 310                 315                 320

Asn Val Pro Asn Met Ser Gln Met Gln Thr Ser Val Gly Ile Val Pro
                325                 330                 335

Thr Gln Ala Ile Ala Thr Gly Pro Thr Ala Asp Pro Glu Lys Arg Lys
            340                 345                 350

Leu Ile Gln Gln Gln Leu Val Leu Leu Leu His Ala His Lys Cys Gln
        355                 360                 365

Arg Arg Glu Gln Ala Asn Gly Glu Val Arg Ala Cys Ser Leu Pro His
    370                 375                 380

Cys Arg Thr Met Lys Asn Val Leu Asn His Met Thr His Cys Gln Ala
385                 390                 395                 400

Gly Lys Ala Cys Gln
                405
```

<210> SEQ ID NO 2
<211> LENGTH: 1290
<212> TYPE: DNA
<213> ORGANISM: Homo sapiens

<400> SEQUENCE: 2

```
cgagccccga ccccgtccg  ggccctcgcc ggccgcgccg cccgtgcccg gggctgtttt       60
cccgagcagg tgaaaatggc tgagaacttg ctggacggac cgcccaaccc caaaagagcc      120
aaactcagct cgcccggttt ctcggcgaat gacagcacag attttggatc attgtttgac      180
ttggaaaatg atcttcctga tgagctgata cccaatggag agaattagg ccttttaaac       240
agtgggaacc ttgttccaga tgctgcttcc aaacataaac aactgtcgga gcttctacga      300
ggaggcagcg gctctagtat caacccagga ataggaaatg tgagcgccag cagccccgtg      360
cagcagggcc tgggtggcca ggctcaaggg cagccgaaca gtgctaacat ggccagcctc      420
agtgccatgg gcaagagccc tctgagccag ggagattctt cagcccccag cctgcctaaa      480
caggcagcca gcacctctgg gcccaccccc gctgcctccc aagcactgaa tccgcaagca      540
caaaagcaag tggggctggc gactagcagc cctgccacgt cacagactgg acctggtatc      600
tgcatgaatg ctaactttaa ccagacccac ccaggcctcc tcaatagtaa ctctggccat      660
agcttaatta atcaggcttc acaagggcag gcgcaagtca tgaatggatc tcttggggct      720
gctggcagag gaagggggagc tggaatgccg taccctactc cagccatgca gggcgcctcg      780
agcagcgtgc tggctgagac cctaacgcag gtttccccgc aaatgactgg tcacgcggga      840
ctgaacaccg cacaggcagg aggcatggcc aagatgggaa taactgggaa cacaagtcca      900
tttggacagc cctttagtca agctggaggg cagccaatgg gagccactgg agtgaacccc      960
cagttagcca gcaaacagag catggtcaac agtttgccca ccttccctac agatatcaag     1020
aatacttcag tcaccaacgt gccaaatatg tctcagatgc aaacatcagt gggaattgta     1080
cccacacaag caattgcaac aggccccact gcagatcctg aaaaacgcaa actgatacag     1140
cagcagctgg ttctactgct tcatgctcat aagtgtcaga gacgagagca agcaaacgga     1200
gaggttcggg cctgctcgct cccgcattgt cgaaccatga aaaacgtttt gaatcacatg     1260
acgcattgtc aggctgggaa agcctgccaa                                      1290
```

<210> SEQ ID NO 3
<211> LENGTH: 468
<212> TYPE: PRT
<213> ORGANISM: Homo sapiens

<400> SEQUENCE: 3

```
Met Val Asp Thr Glu Ser Pro Leu Cys Pro Leu Ser Pro Leu Glu Ala
  1               5                  10                  15

Gly Asp Leu Glu Ser Pro Leu Ser Glu Glu Phe Leu Gln Glu Met Gly
             20                  25                  30

Asn Ile Gln Glu Ile Ser Gln Ser Ile Gly Glu Asp Ser Ser Gly Ser
         35                  40                  45

Phe Gly Phe Thr Glu Tyr Gln Tyr Leu Gly Ser Cys Pro Gly Ser Asp
     50                  55                  60

Gly Ser Val Ile Thr Asp Thr Leu Ser Pro Ala Ser Ser Pro Ser Ser
 65                  70                  75                  80

Val Thr Tyr Pro Val Val Pro Gly Ser Val Asp Glu Ser Pro Ser Gly
                 85                  90                  95
```

```
Ala Leu Asn Ile Glu Cys Arg Ile Cys Gly Asp Lys Ala Ser Gly Tyr
                100                 105                 110
His Tyr Gly Val His Ala Cys Glu Gly Cys Lys Gly Phe Phe Arg Arg
            115                 120                 125
Thr Ile Arg Leu Lys Leu Val Tyr Asp Lys Cys Asp Arg Ser Cys Lys
        130                 135                 140
Ile Gln Lys Lys Asn Arg Asn Lys Cys Gln Tyr Cys Arg Phe His Lys
145                 150                 155                 160
Cys Leu Ser Val Gly Met Ser His Asn Ala Ile Arg Phe Gly Arg Met
                165                 170                 175
Pro Arg Ser Glu Lys Ala Lys Leu Lys Ala Glu Ile Leu Thr Cys Glu
            180                 185                 190
His Asp Ile Glu Asp Ser Glu Thr Ala Asp Leu Lys Ser Leu Ala Lys
        195                 200                 205
Arg Ile Tyr Glu Ala Tyr Leu Lys Asn Phe Asn Met Asn Lys Val Lys
210                 215                 220
Ala Arg Val Ile Leu Ser Gly Lys Ala Ser Asn Asn Pro Pro Phe Val
225                 230                 235                 240
Ile His Asp Met Glu Thr Leu Cys Met Ala Glu Lys Thr Leu Val Ala
                245                 250                 255
Lys Leu Val Ala Asn Gly Ile Gln Asn Lys Glu Val Glu Val Arg Ile
            260                 265                 270
Phe His Cys Cys Gln Cys Thr Ser Val Glu Thr Val Thr Glu Leu Thr
        275                 280                 285
Glu Phe Ala Lys Ala Ile Pro Ala Phe Ala Asn Leu Asp Leu Asn Asp
    290                 295                 300
Gln Val Thr Leu Leu Lys Tyr Gly Val Tyr Glu Ala Ile Phe Ala Met
305                 310                 315                 320
Leu Ser Ser Val Met Asn Lys Asp Gly Met Leu Val Ala Tyr Gly Asn
                325                 330                 335
Gly Phe Ile Thr Arg Glu Phe Leu Lys Ser Leu Arg Lys Pro Phe Cys
            340                 345                 350
Asp Ile Met Glu Pro Lys Phe Asp Phe Ala Met Lys Phe Asn Ala Leu
        355                 360                 365
Glu Leu Asp Asp Ser Asp Ile Ser Leu Phe Val Ala Ala Ile Ile Cys
    370                 375                 380
Cys Gly Asp Arg Pro Gly Leu Leu Asn Val Gly His Ile Glu Lys Met
385                 390                 395                 400
Gln Glu Gly Ile Val His Val Leu Arg Leu His Leu Gln Ser Asn His
                405                 410                 415
Pro Asp Asp Ile Phe Leu Phe Pro Lys Leu Leu Gln Lys Met Ala Asp
            420                 425                 430
Leu Arg Gln Leu Val Thr Glu His Ala Gln Leu Val Gln Ile Ile Lys
        435                 440                 445
Lys Thr Glu Ser Asp Ala Ala Leu His Pro Leu Leu Gln Glu Ile Tyr
    450                 455                 460
Arg Asp Met Tyr
465
```

<210> SEQ ID NO 4
<211> LENGTH: 1854
<212> TYPE: DNA
<213> ORGANISM: Homo sapiens

<400> SEQUENCE: 4

-continued

```
ggcccaggct gaagctcagg gccctgtctg ctctgtggac tcaacagttt gtggcaagac      60
aagctcagaa ctgagaagct gtcaccacag ttctggaggc tgggaagttc aagatcaaag     120
tgccagcaga ttcagtgtca tgtgaggacg tgcttcctgc ttcatagata agagtagctt     180
ggagctcggc ggcacaacca gcaccatctg gtcgcgatgg tggacacgga aagcccactc     240 tgcccctct ccccactcga ggccggcgat ctagagagcc cgttatctga agagttcctg      300
caagaaatgg gaaacatcca agagatttcg caatccatcg gcgaggatag ttctggaagc     360
tttggcttta cggaatacca gtatttagga agctgtcctg gctcagatgg ctcggtcatc     420
acggacacgc tttcaccagc ttcgagcccc tcctcggtga cttatcctgt ggtccccggc     480
agcgtggacg agtctcccag tggagcattg aacatcgaat gtagaatctg cggggacaag     540
gcctcaggct atcattacgg agtccacgcg tgtgaaggct gcaagggctt ctttcggcga     600
acgattcgac tcaagctggt gtatgacaag tgcgaccgca gctgcaagat ccagaaaaag     660
aacagaaaca aatgccagta ttgtcgattt cacaagtgcc tttctgtcgg atgtcacac      720 aacgcgattc gttttggacg aatgccaaga tctgagaaag caaaactgaa agcagaaatt     780
cttacctgtg aacatgacat agaagattct gaaactgcag atctcaaatc tctggccaag     840
agaatctacg aggcctactt gaagaacttc aacatgaaca aggtcaaagc ccgggtcatc     900
ctctcaggaa aggccagtaa caatccacct tttgtcatac atgatatgga gacactgtgt     960
atggctgaga gacgctggt ggccaagctg gtggccaatg catccagaa caaggaggtg     1020 gaggtccgca tctttcactg ctgccagtgc acgtcagtgg agaccgtcac ggagctcacg    1080
gaattcgcca aggccatccc agcgttcgca aacttggacc tgaacgatca agtgacattg    1140
ctaaaatacg gagtttatga ggccatattc gccatgctgt cttctgtgat gaacaaagac    1200
gggatgctgg tagcgtatgg aaatgggttt ataactcgtg aattcctaaa aagcctaagg    1260
aaaccgttct gtgatatcat ggaacccaag tttgattttg ccatgaagtt caatgcactg    1320
gaactggatg acagtgatat ctccctttttt gtggctgcta tcatttgctg tggagatcgt    1380
cctggccttc taaacgtagg acacattgaa aaaatgcagg agggtattgt acatgtgctc    1440
agactccacc tgcagagcaa ccacccggac gatatctttc tcttcccaaa acttcttcaa    1500
aaaatggcag acctccggca gctggtgacg gagcatgcgc agctggtgca gatcatcaag    1560
aagacggagt cggatgctgc gctgcacccg ctactgcagg agatctacag ggacatgtac    1620
tgagttcctt cagatcagcc acaccttttc caggagttct gaagctgaca gcactacaaa    1680
ggagacgggg gagcagcacg attttgcaca aatatccacc actttaacct tagagcttgg    1740
acagtctgag ctgtaggtaa ccggcatatt attccatatc tttgttttaa ccagtacttc    1800
taagagcata gaactcaaat gctggggag gtggctaatc tcaggactgg aag           1854
```

<210> SEQ ID NO 5
<211> LENGTH: 478
<212> TYPE: PRT
<213> ORGANISM: Homo sapiens

<400> SEQUENCE: 5

```
Met Thr Met Val Asp Thr Glu Ile Ala Phe Trp Pro Thr Asn Phe Gly
  1               5                  10                  15

Ile Ser Ser Val Asp Leu Ser Val Met Glu Asp His Ser His Ser Phe
             20                  25                  30

Asp Ile Lys Pro Phe Thr Thr Val Asp Phe Ser Ser Ile Ser Thr Pro
         35                  40                  45
```

```
His Tyr Glu Asp Ile Pro Phe Thr Arg Thr Asp Pro Val Val Ala Asp
    50                  55                  60
Tyr Lys Tyr Asp Leu Lys Leu Gln Glu Tyr Gln Ser Ala Ile Lys Val
 65                  70                  75                  80
Glu Pro Ala Ser Pro Pro Tyr Tyr Ser Glu Lys Thr Gln Leu Tyr Asn
                 85                  90                  95
Lys Pro His Glu Glu Pro Ser Asn Ser Leu Met Ala Ile Glu Cys Arg
            100                 105                 110
Val Cys Gly Asp Lys Ala Ser Gly Phe His Tyr Gly Val His Ala Cys
            115                 120                 125
Glu Gly Cys Lys Gly Phe Phe Arg Arg Thr Ile Arg Leu Lys Leu Ile
        130                 135                 140
Tyr Asp Arg Cys Asp Leu Asn Cys Arg Ile His Lys Lys Ser Arg Asn
145                 150                 155                 160
Lys Cys Gln Tyr Cys Arg Phe Gln Lys Cys Leu Ala Val Gly Met Ser
                165                 170                 175
His Asn Ala Ile Arg Phe Gly Arg Ile Ala Gln Ala Glu Lys Glu Lys
            180                 185                 190
Leu Leu Ala Glu Ile Ser Ser Asp Ile Asp Gln Leu Asn Pro Glu Ser
        195                 200                 205
Ala Asp Leu Arg Gln Ala Leu Ala Lys His Leu Tyr Asp Ser Tyr Ile
    210                 215                 220
Lys Ser Phe Pro Leu Thr Lys Ala Lys Ala Arg Ala Ile Leu Thr Gly
225                 230                 235                 240
Lys Thr Thr Asp Lys Ser Pro Phe Val Ile Tyr Asp Met Asn Ser Leu
                245                 250                 255
Met Met Gly Glu Asp Lys Ile Lys Phe Lys His Ile Thr Pro Leu Gln
            260                 265                 270
Glu Gln Ser Lys Glu Val Ala Ile Arg Ile Phe Gln Gly Cys Gln Phe
        275                 280                 285
Arg Ser Val Glu Ala Val Gln Glu Ile Thr Glu Tyr Ala Lys Ser Ile
    290                 295                 300
Pro Gly Phe Val Asn Leu Asp Leu Asn Asp Gln Val Thr Leu Leu Lys
305                 310                 315                 320
Tyr Gly Val His Glu Ile Ile Tyr Thr Met Leu Ala Ser Leu Met Asn
                325                 330                 335
Lys Asp Gly Val Leu Ile Ser Glu Gly Gln Gly Phe Met Thr Arg Glu
            340                 345                 350
Phe Leu Lys Ser Leu Arg Lys Pro Phe Gly Asp Phe Met Glu Pro Lys
        355                 360                 365
Phe Glu Phe Ala Val Lys Phe Asn Ala Leu Glu Leu Asp Asp Ser Asp
    370                 375                 380
Leu Ala Ile Phe Ile Ala Val Ile Ile Leu Ser Gly Asp Arg Pro Gly
385                 390                 395                 400
Leu Leu Asn Val Lys Pro Ile Glu Asp Ile Gln Asp Asn Leu Leu Gln
                405                 410                 415
Ala Leu Glu Leu Gln Leu Lys Leu Asn His Pro Glu Ser Ser Gln Leu
            420                 425                 430
Phe Ala Lys Leu Leu Gln Lys Met Thr Asp Leu Arg Gln Ile Val Thr
        435                 440                 445
Glu His Val Gln Leu Leu Gln Val Ile Lys Lys Thr Glu Thr Asp Met
    450                 455                 460
```

Ser Leu His Pro Leu Leu Gln Glu Ile Tyr Lys Asp Leu Tyr
465                 470                 475

<210> SEQ ID NO 6
<211> LENGTH: 1811
<212> TYPE: DNA
<213> ORGANISM: Homo sapiens

<400> SEQUENCE: 6

| | | | | | |
|---|---|---|---|---|---|
| ccgacttac | cccaggcggc | cttgacgttg | gtcttgtcgg | caggagacag | caccatggtg | 60 |
| ggttctctct | gagtctggga | attcccgagc | ccgagccgca | gccgccgcct | gggggcttg | 120 |
| ggtcggcctc | gaggacaccg | gagaggggcg | ccacgccgcc | gtggccgcag | aaatgaccat | 180 |
| ggttgacaca | gagatcgcat | tctggcccac | caactttggg | atcagctccg | tggatctctc | 240 |
| cgtaatggaa | gaccactccc | actcctttga | tatcaagccc | ttcactactg | ttgacttctc | 300 |
| cagcatttct | actccacatt | acgaagacat | tccattcaca | gaacagatc | cagtggttgc | 360 |
| agattacaag | tatgacctga | acttcaaga | gtaccaaagt | gcaatcaaag | tggagcctgc | 420 |
| atctccacct | tattattctg | agaagactca | gctctacaat | aagcctcatg | aagagccttc | 480 |
| caactccctc | atggcaattg | aatgtcgtgt | ctgtggagat | aaagcttctg | gatttcacta | 540 |
| tggagttcat | gcttgtgaag | gatgcaaggg | tttcttccgg | agaacaatca | gattgaagct | 600 |
| tatctatgac | agatgtgatc | ttaactgtcg | gatccacaaa | aaagtagaa | ataaatgtca | 660 |
| gtactgtcgg | tttcagaaat | gccttgcagt | ggggatgtct | cataatgcca | tcaggtttgg | 720 |
| gcggatcgca | caggccgaga | aggagaagct | gttggcggag | atctccagtg | atatcgacca | 780 |
| gctgaatcca | gagtccgctg | acctccgtca | ggccctggca | aaacatttgt | atgactcata | 840 |
| cataaagtcc | ttcccgctga | ccaaagcaaa | ggcgagggcg | atcttgacag | aaagacaac | 900 |
| agacaaatca | ccattcgtta | tctatgacat | gaattcctta | atgatgggag | aagataaaat | 960 |
| caagttcaaa | cacatcaccc | ccctgcagga | gcagagcaaa | gaggtggcca | tccgcatctt | 1020 |
| tcagggctgc | cagtttcgct | ccgtggaggc | tgtgcaggag | atcacagagt | atgccaaaag | 1080 |
| cattcctggt | tttgtaaatc | ttgacttgaa | cgaccaagta | actctcctca | aatatggagt | 1140 |
| ccacgagatc | atttacacaa | tgctggcctc | cttgatgaat | aaagatgggg | ttctcatatc | 1200 |
| cgagggccaa | ggcttcatga | caaggagtt | tctaaagagc | ctgcgaaagc | cttttggtga | 1260 |
| ctttatggag | cccaagtttg | agtttgctgt | gaagttcaat | gcactggaat | tagatgacag | 1320 |
| cgacttggca | atatttattg | ctgtcattat | tctcagtgga | gaccgccag | gtttgctgaa | 1380 |
| tgtgaagccc | attgaagaca | ttcaagacaa | cctgctacaa | gccctggagc | tccagctgaa | 1440 |
| gctgaaccac | cctgagtcct | cacagctgtt | tgccaagctg | ctccagaaaa | tgacagacct | 1500 |
| cagacagatt | gtcacggaac | acgtgcagct | actgcaggtg | atcaagaaga | cggagacaga | 1560 |
| catgagtctt | cacccgctcc | tgcaggagat | ctacaaggac | ttgtactagc | agagagtcct | 1620 |
| gagccactgc | caacatttcc | cttcttccag | ttgcactatt | ctgagggaaa | atctgaccat | 1680 |
| aagaaattta | ctgtgaaaaa | gcgttttaaa | agaaaaggg | tttagaatat | gatctatttt | 1740 |
| atgcatattg | tttataaaga | cacatttaca | atttactttt | aatattaaaa | attaccatat | 1800 |
| tatgaaattg | c | | | | | 1811 |

<210> SEQ ID NO 7
<211> LENGTH: 441
<212> TYPE: PRT
<213> ORGANISM: Homo sapiens -continued

<400> SEQUENCE: 7

```
Met Glu Gln Pro Gln Glu Ala Pro Glu Val Arg Glu Glu Glu
  1               5                  10                  15
Lys Glu Glu Val Ala Glu Ala Glu Gly Ala Pro Glu Leu Asn Gly Gly
                 20                  25                  30
Pro Gln His Ala Leu Pro Ser Ser Tyr Thr Asp Leu Ser Arg Ser
             35                  40                  45
Ser Ser Pro Pro Ser Leu Leu Asp Gln Leu Gln Met Gly Cys Asp Gly
 50                  55                  60
Ala Ser Cys Gly Ser Leu Asn Met Glu Cys Arg Val Cys Gly Asp Lys
 65                  70                  75                  80
Ala Ser Gly Phe His Tyr Gly Val His Ala Cys Glu Gly Cys Lys Gly
                 85                  90                  95
Phe Phe Arg Arg Thr Ile Arg Met Lys Leu Glu Tyr Glu Lys Cys Glu
                100                 105                 110
Arg Ser Cys Lys Ile Gln Lys Lys Asn Arg Asn Lys Cys Gln Tyr Cys
                115                 120                 125
Arg Phe Gln Lys Cys Leu Ala Leu Gly Met Ser His Asn Ala Ile Arg
            130                 135                 140
Phe Gly Arg Met Pro Glu Ala Glu Lys Arg Lys Leu Val Ala Gly Leu
145                 150                 155                 160
Thr Ala Asn Glu Gly Ser Gln Tyr Asn Pro Gln Val Ala Asp Leu Lys
                165                 170                 175
Ala Phe Ser Lys His Ile Tyr Asn Ala Tyr Leu Lys Asn Phe Asn Met
            180                 185                 190
Thr Lys Lys Lys Ala Arg Ser Ile Leu Thr Gly Lys Ala Ser His Thr
            195                 200                 205
Ala Pro Phe Val Ile His Asp Ile Glu Thr Leu Trp Gln Ala Glu Lys
210                 215                 220
Gly Leu Val Trp Lys Gln Leu Val Asn Gly Leu Pro Pro Tyr Lys Glu
225                 230                 235                 240
Ile Ser Val His Val Phe Tyr Arg Cys Gln Cys Thr Thr Val Glu Thr
                245                 250                 255
Val Arg Glu Leu Thr Glu Phe Ala Lys Ser Ile Pro Ser Phe Ser Ser
            260                 265                 270
Leu Phe Leu Asn Asp Gln Val Thr Leu Leu Lys Tyr Gly Val His Glu
            275                 280                 285
Ala Ile Phe Ala Met Leu Ala Ser Ile Val Asn Lys Asp Gly Leu Leu
290                 295                 300
Val Ala Asn Gly Ser Gly Phe Val Thr Arg Glu Phe Leu Arg Ser Leu
305                 310                 315                 320
Arg Lys Pro Phe Ser Asp Ile Ile Glu Pro Lys Phe Glu Phe Ala Val
                325                 330                 335
Lys Phe Asn Ala Leu Glu Leu Asp Asp Ser Asp Leu Ala Leu Phe Ile
            340                 345                 350
Ala Ala Ile Ile Leu Cys Gly Asp Arg Pro Gly Leu Met Asn Val Pro
            355                 360                 365
Arg Val Glu Ala Ile Gln Asp Thr Ile Leu Arg Ala Leu Glu Phe His
            370                 375                 380
Leu Gln Ala Asn His Pro Asp Ala Gln Tyr Leu Phe Pro Lys Leu Leu
385                 390                 395                 400
Gln Lys Met Ala Asp Leu Arg Gln Leu Val Thr Glu His Ala Gln Met
                405                 410                 415
```

Met Gln Arg Ile Lys Lys Thr Glu Thr Glu Thr Ser Leu His Pro Leu
            420                 425                 430

Leu Gln Glu Ile Tyr Lys Asp Met Tyr
        435                 440

<210> SEQ ID NO 8
<211> LENGTH: 3301
<212> TYPE: DNA
<213> ORGANISM: Homo sapiens
<220> FEATURE:
<221> NAME/KEY: misc_feature
<222> LOCATION: (1)...(3301)
<223> OTHER INFORMATION: n = A,T,C or G

<400> SEQUENCE: 8

```
gaattctgcg gagcctgcgg gacggcggcg ggttggcccg taggcagccg ggacagtgtt      60
gtacagtgtt ttgggcatgc acgtgatact cacacagtgg cttctgctca ccaacagatg     120
aagacagatg caccaacgag ggtctggaat ggtctggagt ggtctggaaa gcagggtcag     180
ataccctgg aaaactgaag cccgtggagc aatgatctct acaggactgc ttcaaggctg      240
atgggaacca ccctgtagag gtccatctgc gttcagaccc agacgatgcc agagctatga     300
ctgggcctgc agtgtggcg ccgaggggag atcagccatg gagcagccac aggaggaagc      360
ccctgaggtc cgggaagagg aggagaaaga ggaagtggca gaggcagaag gagccccaga     420
gctcaatggg ggaccacagc atgcacttcc ttccagcagc tacacagacc tctcccggag     480
ctcctcgcca ccctcactgc tggaccaact gcagatgggc tgtgacgggg cctcatgcgg     540
cagcctcaac atggagtgcc gggtgtgcgg ggacaaggca tcgggcttcc actacggtgt     600
tcatgcatgt gagggtgca agggcttctt ccgtcgtacg atccgcatga agctggagta      660
cgagaagtgt gagcgcagct gcaagattca agaagaagaac cgcaacaagt gccagtactg     720
ccgcttccag aagtgcctgg cactgggcat gtcacacaac gctatccgtt ttggtcggat     780
gccggaggct gagaagagga agctggtggc agggctgact gcaaacgagg ggagccagta     840
caacccacag gtggccgacc tgaaggcctt ctccaagcac atctacaatg cctacctgaa     900
aaacttcaac atgaccaaaa agaaggcccg cagcatcctc accggcaaag ccagccacac     960
ggcgcccttt gtgatccacg acatcgagac attgtggcag cagagaagg ggctggtgtg    1020
gaagcagttg gtgaatggcc tgcctcccta caaggagatc agcgtgcacg tcttctaccg    1080
ctgccagtgc accacagtgg agaccgtgcg ggagctcact gagttcgcca agagcatccc    1140
cagcttcagc agcctcttcc tcaacgacca ggttacccct ctcaagtatg gcgtgcacga    1200
ggccatcttc gccatgctgg cctctatcgt caacaaggac gggctgctgg tagccaacgg    1260
cagtggcttt gtcacccgtg agttcctgcg cagcctccgc aaaccttca gtgatatcat     1320
tgagcctaag tttgaatttg ctgtcaagtt caacgccctg gaacttgatg acagtgacct    1380
ggccctattc attgcggcca tcattctgtg tggagaccgg ccaggcctca tgaacgttcc    1440
acgggtggag gctatccagg acaccatcct gcgtgccctc gaattccacc tgcaggccaa    1500
ccaccctgat gcccagtacc tcttccccaa gctgctgcag aagatggctg acctgcggca    1560
actggtcacc gagcacgccc agatgatgca gcggatcaag aagaccgaaa ccgagacctc    1620
gctgcaccct ctgctccagg agatctacaa ggacatgtac taacggcggc acccaggcct    1680
ccctgcagac tccaatgggg ccagcactgg aggggcccac ccacatgact ttccattga    1740
ccagctctct tcctgtcttt gttgtctccc tctttctcag ttcctctttc ttttctaatt    1800
```

-continued

```
cctgttgctc tgtttcttcc tttctgtagg tttctctctt cccttctccc ttctcccttg    1860
ccctcccttt ctctctccta tccccacgtc tgtcctcctt tcttattctg tgagatgttt    1920
tgtattattt caccagcagc atagaacagg acctctgctt ttgcacacct tttccccagg    1980
agcagaagag agtgggcctg ccctctgccc catcattgca cctgcaggct taggtcctca    2040
cttctgtctc ctgtcttcag agcaaaagac ttgagccatc caaagaaaca ctaagctctc    2100
tgggcctggg ttccagggaa ggctaagcat ggcctggact gactgcagcc ccctatagtc    2160
atggggtccc tgctgcaaag gacagtggca gaccccggca gtagagccga gatgcctccc    2220
caagactgtc attgccccctc cgatcgtgag gccacccact gacccaatga tcctctccag    2280
cagcacacct cagccccact gacacccagt gtccttccat cttcacactg gtttgccagg    2340
ccaatgttgc tgatggcccc tccagcacac acacataagc actgaaatca ctttacctgc    2400
aggcaccatg cacctccctt ccctccctga ggcaggtgag aacccagaga gaggggcctg    2460
caggtgagca ggcagggctg ggccaggtct ccggggaggc aggggtcctg caggtcctgg    2520
tgggtcagcc cagcacctcg cccagtggga gcttcccggg ataaactgag cctgttcatt    2580
ctgatgtcca tttgtcccaa tagctctact gccctcccct tccctttac tcagcccagc     2640
tggccaccta gaagtctccc tgcacagcct ctagtgtccg gggaccttgt gggaccagtc    2700
ccacaccgct ggtccctgcc ctcccctgct cccaggttga ggtgcgctca cctcagagca    2760
gggccaaagc acagctgggc atgccatgtc tgagcggcgc agagccctcc aggcctgcag    2820
gggcaagggg ctggctggag tctcagagca cagaggtagg agaactgggg ttcaagccca    2880
ggcttcctgg gtcctgcctg gtcctccctc ccaaggagcc attctatgtg actctgggtg    2940
gaagtgccca gccctgcct gacggnnnnn nngatcactc tctgctggca ggattcttcc     3000
cgctccccac ctacccagct gatgggggtt ggggtgcttc tttcagccaa ggctatgaag    3060
ggacagctgc tgggacccac ctccccccctt ccccggccac atgccgcgtc cctgccccca   3120
cccgggtctg gtgctgagga tacagctctt ctcagtgtct gaacaatctc caaaattgaa    3180
atgtatattt ttgctaggag ccccagcttc ctgtgttttt aatataaata gtgtacacag    3240
actgacgaaa ctttaaataa atgggaatta aatatttaaa aaaaaagcg gccgcgaatt    3300
c                                                                   3301
```

<210> SEQ ID NO 9
<211> LENGTH: 38
<212> TYPE: DNA
<213> ORGANISM: Homo sapiens

<400> SEQUENCE: 9
actcggatcc aagccatggc tgagaacttg ctggacgg                           38

<210> SEQ ID NO 10
<211> LENGTH: 32
<212> TYPE: DNA
<213> ORGANISM: Homo sapiens

<400> SEQUENCE: 10
cacaaagctt aggccatgtt agcactgttc gg                                 32

<210> SEQ ID NO 11
<211> LENGTH: 37
<212> TYPE: DNA
<213> ORGANISM: Homo sapiens

<400> SEQUENCE: 11

```
ctcagtcgac ttattgaatt ccactagctg gagatcc                                    37
```

<210> SEQ ID NO 12
<211> LENGTH: 5
<212> TYPE: PRT
<213> ORGANISM: Homo sapiens
<220> FEATURE:
<221> NAME/KEY: VARIANT
<222> LOCATION: (1)...(5)
<223> OTHER INFORMATION: Xaa = Any Amino Acid

<400> SEQUENCE: 12

```
Leu Xaa Xaa Leu Leu
 1               5
```